United States Patent [19]

Nisbet et al.

[11] Patent Number: 5,478,557
[45] Date of Patent: Dec. 26, 1995

[54] PROBIOTIC FOR CONTROL OF SALMONELLA

[75] Inventors: David J. Nisbet; Donald E. Corrier; John R. DeLoach, all of College Station, Tex.

[73] Assignee: The United States of America, as represented by the Secretary of Agriculture, Washington, D.C.

[21] Appl. No.: 166,779

[22] Filed: Dec. 13, 1993

Related U.S. Application Data

[63] Continuation-in-part of Ser. No. 921,173, Jul. 29, 1992, Pat. No. 5,340,577.

[51] Int. Cl.$^6$ .................................................. A61K 35/74
[52] U.S. Cl. ................. 424/93.21; 424/93.3; 424/93.45; 424/93.46; 424/93.48
[58] Field of Search ............................. 424/93 D, 93 J, 424/93 K, 93 R, 93.21, 93.3, 93.45, 93.46, 93.48, 93.4; 514/35

[56] References Cited

U.S. PATENT DOCUMENTS

| | | | |
|---|---|---|---|
| 3,937,814 | 2/1976 | Nickerson et al. | 424/93 |
| 3,953,609 | 4/1976 | Farr | 426/2 |
| 4,335,107 | 6/1982 | Snoeyenbos et al. | 424/93 |
| 4,689,226 | 8/1987 | Nurmi et al. | 424/93 |
| 5,308,615 | 5/1994 | DeLoach et al. | 424/93 C |
| 5,322,686 | 6/1994 | Grahn et al. | 424/93 H |

OTHER PUBLICATIONS

Nisbet, David J., et al., "Effect of Mixed Cecal Microflora Maintained in Continuous Culture and of Dietary Lactose on *Salmonella typhimurium* Colonization in Broiler Chicks", *Avian Diseases*, 37, 1993, pp. 528–535.

Nisbet, David J., et al., "Effect of a Defined Continuous Flow Derived Bacterial Culture and Dietary lactose on *Salmonella typhimurium* Colonization in Broiler Chickens", *Avian Diseases*, 37, 1993, pp. 1017–1025.

Nisbet, David J., et al., "Method for Selecting Poultry Microorganisms Inhibitory tp Salmonella", 43rd North Central Avian Disease Conference, Oct. 4–6, 1992, Minneapolis, Minn.

Freter, Rolf, et al., "Mechanisms That Control Bacterial Populations in Continuous–Flow Culture Models of Mouse Large Intestinal Flora", *Infection and Immunity*, Feb. 1983, vol. 32, No. 2, pp. 676–685.

Freter, Rolf et al., "Continuous–Flow Cultures as In Vitro Models of the Ecology of Large Intestinal Flora", *Infection and Immunity*, Feb. 1983, vol. 39, No. 2, pp. 666–675.

Freter, Rolf, "Factors affecting the microecology of the gut", in *Probiotics The Scientific Basis* by Roy Fuller, Chapman & Hall, published Jun. 1992, pp. 111–144.

Corrier D. E., et al., "Decreased Salmonella Colonization in Turkey Poults Inoculated with Anaerobic Cecal Microflora and Provided Dietary Lactose", 1991, *Poultry Science*, 70, pp. 1345–1350.

Hinton, Arthur, et al., "Environment and Health Comparison of the Efficacy of Cultures of Cecal Anaerobes as Inocular to Reduce *Salmonella typhimurium* Colonization in Chicks With or Without Dietary Lactose", 1991, *Poultry Science*, 70, pp. 67–73.

Corrier, Donald E., et al., "Effect of Anaerobic Cecal Microflora and Dietary Lactose on Colonization Resistance of Layer Chicks to Invasive *Salmonella enteritidis*", *Avian Disease*, 35, 1991, pp. 337–343.

Hinton, Arthur Jr., et al., "In Vitro Inhibition of the Growth of *Salmonella typhimurium* by Bacteria Isolated From the Cecal Contents of Mature Chickens", Abstracts, Twelfth Annual Meeting of the Southern Poultry Science Society, Atlanta, Ga., Jan. 28–29, 1991.

Hinton, A. Jr., et al., "Inhibition of the Growth of *Escherichia coli* 015:H7 by Bacteria Isolated from Chickens", Abstracts, IFT Annual Meeting & Food Expo, Dallas, Tex., Jun. 1–5, 1991.

Hinton, Arthur Jr., et al., "In Vitro Inhibition of the Growth of *Salmonella Typhimurium*, and *Escherichia coli* 0157:H7 by Bacteria Isolated from the Cecal Contents of Adult Chickens", *Journal of Food Protecion*, vol. 54, Jul. 1991, pp. 495–601.

Hinton, Arthur Jr., et al., "Biological Control of *Salmonella typhimurium* in Young Chickens", *Avian Diseases*, 34, 1990, pp. 626–633.

Corrier, Donald E., et al., "Effect of Dietary Lactose on Cecal pH, Bacteriostatic Volatile Fatty Acids, and *Salmonella typhimurium* Colonization of Broiler Chicks", *Avian Diseases*, 34, 1990, pp. 617–625.

Corrier, Donald E., et al., "Effect of Dietary Lactose on Salmonella Colonization of Market–Age Broiler Chickens", *Avian Diseases*, 34, 1990, pp. 668–676.

Ziprin, Richard L., et al., "Intracloacal *Salmonella typhimurium* Infection of Broiler Chickens: Reduction of Colonization with Anaerobic Organisms and Dietary Lactose", *Avian Diseases*, 34, 1990, pp. 749–753.

(List continued on next page.)

*Primary Examiner*—Raymond Henley, III
*Assistant Examiner*—Kevin E. Weddington
*Attorney, Agent, or Firm*—M. Howard Silverstein; Randall E. Deck; John D. Fado

[57] ABSTRACT

A defined probiotic or composition of anaerobic bacteria effective for controlling or inhibiting Salmonella colonization of fowl. The probiotic includes populations or cultures of 29 substantially biologically pure bacteria. In use, the probiotic is administered to the subject fowl in an amount effective for increasing resistance to Salmonella colonization thereof.

The invention also relates to a novel method for isolating probiotics which are effective for controlling or inhibiting Salmonella colonization of domestic animals, from fecal droppings, cecal contents or large intestines of the adult animals. The droppings, cecal contents or large intestine are combined with a culture medium and incubated without dilution (i.e. batch culture) under anaerobic conditions. Following this preliminary incubation, the resultant culture is subjected to continuous flow conditions until a steady state is achieved, after which time the steady state culture may be recovered for use as a probiotic.

29 Claims, No Drawings

OTHER PUBLICATIONS

Oyofo, Buhari A., et al., "Effect of Carbohydrates on *Salmonella typhimurium* Colonization in Broiler Chickens", *Avian Diseases*, 33, 1989, pp. 531–534.

Stavric, S., et al., "Competitive Exclusion of Salmonella from Newly Hatched Chicks by Mixtures of Pure Bacterial Cultures Isolated from Fecal and Cecal Contents of Adult Birds", *Journal of Food Protection*, vol. 48, No. 9, Sep. 1989, pp. 778–782.

Hinton, M., et al., "Salmonella Control in Poultry: The Need for the Satisfactory Evaluation of Probiotics for this Purpose", *Letters in Applied Microbiology*, 13, 1991, pp. 49–50.

Nisbet, David J., et al., "Effect of Mixed Cecal Microflora Maintained in Continuous Culture and of Dietary Lactose on *Salmonella typhimurium* Colonization in Broiler Chicks", *Avian Diseases*, 37, 1993, pp. 528–535.

Corrier, D. E., et al., "Development of Defined Cultures of Indigenous Cecal Bacteria to Control Salmonellosis in Broiler Chicks", *Poultry Science*, 72, 1993, pp. 1164–1168.

Nisbet, David J., et al., "Effect of a Defined Continuous–Flow Derived Bacterial Culture and Dietary Lactose on *Salmonella typhimurium* Colonization in Broiler Chicks", *Avian Diseases*, 37, 1993, pp. 1017–1025

Nisbet, David J., et al., "Inoculation of Broiler Chicks with a Continuous–flow Derived Bacterial Culture Facilitates Early Cecal Bacterial Colonization and Increases Resistance to *Salmonella typhimurium*", *Journal of Food Protection*, vol. 57, No. 1, pp. 12–15 (Jan. 1994).

Corrier, David J., et al., "Effect of Dietary Lactose and Cell Concentration on the Ability of a Continuous–Flow–Derived Bacterial Culture to Control Salmonella Cecal Colonization in Broiler Chickens", *Poultry Science*, 73, 1994, pp. 56–62.

PROBIOTIC FOR CONTROL OF SALMONELLA

CROSS-REFERENCE TO RELATED APPLICATIONS

This is a continuation-in-part of U.S. application Ser. No. 07/921,173, filed Jul. 29, 1992, now U.S. Pat. No. 5,340,577 the contents of which are incorporated by reference herein.

BACKGROUND OF THE INVENTION

1. Field of the Invention

This invention relates to defined probiotics for the control of Salmonella colonization in domestic animals including fowl, and particularly chickens.

Despite the efforts of researchers and public health agencies, the incidence of human salmonellosis has increased over the past 20 years. The number of actual reported cases of human Salmonella infection exceeds 40,000 per year. However, the Communicable Disease Center estimates that the true incidence of human Salmonella infections in the U.S. each year may be as high as 2 to 4 million. Animal food products, including poultry, remain the principal source of human infection.

2. Description of the Prior Art

Considering the widespread presence of Salmonella in the environment, it is unlikely that poultry can be completely protected from Salmonella exposure. Therefore, researchers have continued to investigate means of increasing resistance to colonization in poultry exposed to Salmonella. Studies have focused on the evaluation of vaccines, establishment of protection normal intestinal flora, and the identification of feed additives that will inhibit Salmonella growth and colonization. The role of host immunity against Salmonella colonization is unclear, and it also remains uncertain if stimulation of immune responses will effectively enhance colonization resistance. Experimental vaccines have not proven to be consistently effective.

It is well documented that normal intestinal microflora increase resistance against Salmonella colonization. Oral inoculation of young chicks with anaerobic bacterial cultures of microflora, also known as probiotics (defined as bacterial cultures which have a beneficial effect on the animal to which they are administered), prepared from the cecal contents or fecal droppings of mature chickens has proven to effectively reduce Salmonella colonization [Shoeyenbos et al., Avian Dis., 23:904–913, (1979), Schneitz et al., Acta Pathol. Microbiol. Scand. Sect. B., 89:109–116, (1981), and Stavric et al., J. Food Prot., 48:778–782, (1985)]. Conversely, poultry rearing practices that prevent chicks from becoming colonized by these cecal anaerobes make the chicks more susceptible to Salmonella colonization [Pivnick et al., J. Food Prot., 44:909–916, (1981)]. These probiotics may decrease Salmonella colonization by rapidly colonizing the intestinal tract of the young chicks (Pivnick et al., ibid), by competing for attachment sites on the intestinal wall (Snoeyenbos et al., ibid), or by producing bacteriostatic or bactericidal short-chained volatile fatty acids [Barnes et al., J. Hyg. Camb., 82:263–183, (1979) and Am. J. Clin. Nutr., 33:2426–1433, (1980), Corrier et al., Avian Dis., 34:668–676, (1990) and Avian Dis., 34:617–625, (1990), and Hinton et al., Avian Dis., 34:626–633, (1990)] that inhibit the growth of enteropathogens.

However, only cultures of normal microflora that contain a mixed population of several hundred different microorganisms have proven to effectively inhibit Salmonella growth. Establishment of normal intestinal flora in day-old chicks using mixed cultures of micro-organisms has been widely used to control Salmonella colonization in several European countries. Yet, because of the undefined number and types of micro-organisms present in mixed cultures, the system has not been widely accepted in the United States. One drawback to the widespread use of the this method has been the fact that the composition of the product cannot be standardized, and thus the product cannot be stored or produced on a large scale without changes in composition and effectiveness. Also, because the starting material is always the intestinal content of an adult fowl, the product may contain pathogenic viruses, bacteria, or parasites, which may be dangerous to the health of the chicks. Further still, the U.S. Food & Drug Administration has recently required that all undefined cultures must be approved.

Lactose and other milk sugar products added to the feed or water of chicks have recently been reported to enhance resistance against Salmonella colonization [Oyofo et al., Avian Dis., 33:531–534, (1989) and Poultry Sci., 68:1357–1360, (1989), Corrier et al., ibid, and Hinton et al., ibid.]. Dietary lactose increases the acidity of the cecal contents and influences the growth and fermentation products of normal intestinal microflora. Lactose supplemented diets may also enhance Salmonella colonization resistance by increasing the bacteriostatic action of short chain volatile fatty acids such as acetic, propionic, and butyric acids, produced by some normal intestinal bacterial [Corrier et al., ibid, Hinton et al., ibid].

Resistance to Salmonella colonization in chicks has also further been increased when the chicks are provided the combination of dietary lactose and cultures of cecal anaerobes grown in a lactose containing broth [Corrier et al. and Hinton et al., ibid].

SUMMARY OF THE INVENTION

We have now discovered a defined probiotic or composition of bacteria effective for controlling or inhibiting Salmonella colonization of fowl. The probiotic is comprised of defined populations or cultures of substantially biologically pure bacteria. These include strains of the following bacteria:
*Enterococcus faecalis,*
*Enterococcus faecium,*
*Enterococcus avium,*
*Lactococcus lactis,*
Lactobacillus,
*Escherichia coli,*
*Citrobacter freundii,*
Pseudomonas,
*Serratia liquefaciens,*
Propionibacterium,
Bifidobacterium (or Lactobacillus),
Eubacterium,
Veillonella, and
Fusobacterium,
as well as another bacterium belonging to the family Enterobacteriaceae, and an unknown bacterium designated strain OAGPB-5.

In use, the probiotic is administered to the subject fowl in an amount effective for inhibiting Salmonella colonization thereof. In a preferred embodiment, enhanced inhibition of Salmonella may be achieved by incorporation of lactose into the probiotic. The above-mentioned probiotic may also be combined with a conventional feed, providing a novel feed product which may be orally ingested by the fowl.

The invention also relates to a novel method for isolating probiotics which are effective for controlling or inhibiting Salmonella colonization of domestic animals, including fowl, from fecal droppings or cecal or large intestine contents of the adult animals. The droppings or cecal or intestine contents are combined with a nutrient or culture medium and incubated without dilution (i.e. batch culture) under anaerobic conditions. Following this preliminary incubation, the resultant culture is subjected to continuous flow conditions until a steady state is achieved, after which time the steady state culture may be recovered for use as a probiotic.

In accordance with this discovery, it is an object of this invention to provide an improved method and composition for controlling Salmonella colonization in fowl.

A further object of this invention is to provide defined cultures of anaerobic bacteria for controlling Salmonella colonization in fowl which may be easily standardized.

Yet another object is to provide an improved method for isolating compositions of bacteria for use as probiotics for controlling Salmonella colonization in domestic animals, particularly fowl.

Other objects and advantages of this invention will become obvious from the ensuing description.

DETAILED DESCRIPTION OF THE INVENTION

The probiotic of this invention is effective for controlling Salmonella colonization of fowl when administered thereto, reducing the average Salmonella concentration in the fowl population and/or lowering the percentage fowl colonized by the pathogen. The invention may be practiced with any type of fowl, including but not limited to poultry such as chickens, turkeys, ducks, quail and geese. Upon administration to fowl, the probiotic provides consistent protection against a variety of Salmonella, especially *S. typhimurium* and *S. enteriditis*.

The probiotic was developed from the ceca of Salmonella-free chickens. As described in more detail in Example 1, the ceca from the chickens were recovered, inoculated into the suitable culture medium, and incubated under anaerobic conditions in a batch culture. The culture was then incubated under continuous-flow culture conditions at a specified media turnover until a steady-state or equilibrium was achieved. When recovered and administered to fowl, the resultant steady state culture demonstrated significant effectiveness as a probiotic for the control of Salmonella colonization of the treated birds.

Upon analysis, 29 substantially pure bacterial isolates were recovered from the steady state culture, including 15 facultative and 14 obligate anaerobes. The composition of the culture was determined as follows:

I. *Facultative anaerobic, gram positive cocci:*
  (1) a first *Enterococcus faecalis* strain,
  (2) a second *Enterococcus faecalis* strain,
  (3) first *Enterococcus faecium* strain,
  (4) a second *Enterococcus faecium* strain,
  (5) a third *Enterococcus faecium* strain,
  (6) *Enterococcus avium*,
  (7) a third *Enterococcus faecalis* strain, II. *Facultative anaerobic,* gram-positive coccobacilli:
  (8) *Lactococcus lactis*,
  (9) a first Lactobacillus strain, III. *Facultative anaerobic,* gram negative bacilli:
  (10) a first *Escherichia coli* strain,
  (11) *Citrobacter freundii*,
  (12) a bacterium belonging to the family Enterobacteriaceae,
  (13) a Pseudomonas species,
  (14) *Serratia liquefaciens*,
  (15) a second *Escherichia coli* strain, IV. Obligate anaerobic, gram positive bacilli:
  (16) a first Propionibacterium species,
  (17) a second Propionibacterium species,
  (18) a second Lactobacillus strain,
  (19) a first Bifidobacterium strain or a third Lactobacillus strain,
  (20) a third Propionibacterium strain,
  (21) a first Eubacterium strain,
  (22) a second Eubacterium strain,
  (23) an unknown bacterium designated strain OAGPB-5,
  (24) a third Eubacterium strain,
  (25) a second Bifidobacterium strain or a fourth Lactobacillus strain,
  (26) a third Bifidobacterium strain or a fifth Lactobacillus strain,
  (27) a fourth Propionibacterium strain, V. Obligate anaerobic, gram negative cocci:
  (28) a Veillonella species, and VI. Obligate anaerobic, gram-negative bacilli:
  (29) a Fusobacterium species.

A probiotic composition, including all 29 of the above-mentioned bacterial strains, has been deposited under the Budapest Treaty on Nov. 24, 1994 in the American Type Culture Collection (12301 Parklawn Drive, Rockville, Md. 20852, USA) as Competitive Exclusion Culture, CF3, and has been assigned Deposit No. ATCC 55515. The individual strains are characterized in Examples 1 and 2.

The resultant steady state culture may be used directly as a probiotic, or stored for later use. With respect to the latter, the culture may be stored as a mixture as indicated, or the individual bacteria may isolated, stored and subsequently recombined.

In accordance with the preferred embodiment, the probiotic is composed of bacteria from the deposited steady state culture referred to in Examples 1 and 2. However, in an alternative embodiment, many of the bacteria to be used may be obtained from known or standard strains, or from isolates recovered from fowl. For example, without being limited thereto, one or more other strains of Enterococcus, Lactococcus, *E. coli*, Citrobacter, Pseudomonas, Serratia, Propionibacterium, Bifidobacterium, Eubacterium, Veillonella, Fusobacterium or particularly Lactobacillus, may be substituted for the strains of the same genus or species in the deposited probiotic of the Examples. To enhance efficacy when using stock cultures of known strains, the bacteria may be adapted to the fowl by passage therethrough, preferably together with the other organisms from the steady state culture, followed by their subsequent retrieval and isolation from droppings or cecal contents. When fowl isolates are used, the bacteria maybe individually isolated and recovered from fecal droppings or cecal contents of adult fowl using techniques conventional in the art or as described by DeLoach [U.S. patent application Ser. No. 07/822,505], the contents of which are incorporated by reference herein.

It is also envisioned that this invention may be practiced with a probiotic having fewer than all 29 of the above-mentioned bacterial strains, and that one, two or three of the bacteria may be removed from the probiotic with only a slight decrease in efficacy. For example, without being limited thereto, the Pseudomonas or strains of bacteria which are redundant, that is those genera having multiple strains or species present, may be deleted without significantly decreasing efficacy. However, in accordance with the preferred embodiment, optimal control of Salmonella colonization is achieved with a probiotic which includes all 29 strains.

Some of the strains of the bacteria of this invention may also be optionally selected for the ability to adhere to the epithelial cells of the alimentary tract of the subject fowl in accordance with the technique of Nurmi et al., U.S. Pat. No. 4,689,226, the contents of which are incorporated by reference herein.

This invention also relates to a novel process for obtaining probiotics effective for controlling or inhibiting Salmonella colonization of a variety of domestic animals, including but not limited to fowl and also equine, porcine and bovine. Rather than producing a probiotic form known stock cultures or pure bacterial isolates, we have unexpectedly discovered that a stable, defined probiotic may be produced directly from fecal droppings, cecal and/or large intestine contents of the adult target animal. In accordance with this method, the droppings or cecal or large intestine contents are first used as inoculum for a batch culture, and then cultured under continuous flow conditions at a specified media turnover and pH until a steady state or equilibrium is attained. The resultant steady state culture may be recovered for use as a probiotic. The term cecal contents is defined herein to encompass material within the inner confines of the cecum, as well as the entire cecum per se, including portions thereof such as the mucous layer.

The batch culture stage may be conducted in any conventional fermenter. However, use of a chemostat without dilution (i.e. without addition of fresh culture medium and removal of spent culture medium) is preferred to eliminate transfer of the culture for subsequent steps, and to reduce potential contamination of the culture. After their collection, the cecal or large intestine contents form the animal or its droppings, which are to be used as inoculum, are combined with a suitable culture medium and incubated under anaerobic conditions. This batch culture should be continued:

(1) for about 6–18 hours, preferably about 12–18 hours, or (2) until the optical density (measured at 600 nm) reaches at least about 1.0, and/or (3) for no more than about 2 hours after the pH reaches about 4.2;

after which time the batch culture should be terminated and continuous culture initiated. When the incubation period is determined by condition (1) or particularly condition (2), it is preferred to control the pH at about 5.5 using a pH controller as is conventional in the art. Further, in the event that this pH control is not employed, to avoid death of some of the cells, it is preferred that the batch culture should be continued to a pH no less than about 4.2.

Continuous culture in a chemostat, with continuous supply of fresh medium and removal of spent broth, is than initiated immediately following conclusion of the batch culture stage. Suitable chemostats may be readily determined and include, for example, those described by Wang [Fermentation and Enzyme Technology, John Wiley & sons, New York, 1979, pages 98–137, the contents of which are incorporated by reference herein]. Surprisingly, growth of the mixture in continuous culture with a specific dilution or media turnover rate and at a specific pH allows the culture to come to an equilibrium or steady state. Depending upon the animal used as the inoculum source, the specific media and culture conditions, the number of bacteria originally present may be reduced to a stable culture of relatively few substantially biologically pure bacteria which may be readily defined. For example, when using fowl, the approximately 500 bacteria originally present in the inoculum may be reduced to a stable culture of about 10 to 40 bacteria. Suitable conditions for this stage include a turnover rate between about 0.029 to about 0.10 $hr^{-1}$, preferably about 0.0416 $hr^{-1}$, and a pH between about 4.7 to 6.5, preferably about 5.5.

The temperature and media used for the batch and continuous cultures are not critical and may be readily determined. Suitable temperatures may vary between about 26° to 47° C. A variety of suitable culture media having different energy sources may also be used. Without being limited thereto, preferred energy sources include glucose or galactose and particularly lactose.

A steady state may be assumed when culture pH, $OD_{600}$ and volatile fatty acid concentrations remain approximately constant. Once a steady state is achieved, the culture may be recovered at any time for use as described. Ideally, the steady state culture should also be characterized or defined, isolating and identifying the bacterial populations therein using techniques conventional in the art. Once isolated, the bacteria may be stored indefinitely using conventional techniques for later use as described, for instance, in U.S. patent application Ser. No. 07/921,173, filed Jul. 29, 1992. The practitioner skilled in the art will recognize that the above-described batch/continuous culture process may also be employed using isolated or biologically pure bacteria as initial inoculum.

Steady state cultures produced in accordance with this process may be optionally screened to select those compositions which demonstrate optimal efficacy for the inhibition Salmonella colonization of the target animal. In one embodiment, screening may be conducted in vivo with Salmonella challenge as is conventional in the art and described in Examples 3 and 4. Briefly, the steady state culture is administered to Salmonella-free animals as described herein. After a period of time sufficient for the culture to become established in the gut, usually after day 2 or 3, the animals are challenged with a viable culture of Salmonella, incubated, and subsequently killed and the cecal contents analyzed for Salmonella colonization. Effective inhibition of Salmonella colonization is indicated by a reduced average Salmonella concentration (CFU), or a lower percentage of animals colonized, in the treated population relative to an untreated control.

We have also discovered that the probiotics produced in accordance with this invention, or by any other process, may also be accurately screened in vivo by analysis of the volatile fatty acid (VFA) profile in the cecum. This technique does not require the customary Salmonella challenge. To evaluate the efficacy of any culture, it is administered to a target animal, and the culture allowed to become established in the gut as before. About 2–3 days after treatment, preferably at 3 days, the animals are sacrificed and the propionic acid and total volatile fatty acid (acetic plus propionic, butyric, isobutyric, valeric and isovaleric acids) concentration in the cecal contents are determined. Techniques which may be used for the measurement of the acids are conventional in the art and include gas-liquid chromatography as described by Corrier et al. (Avian Dis., 34:617–625, 1990), the contents of which are incorporated by reference herein. Efficacy as a probiotic for the inhibition of Salmonella colonization is indicated when:

(1) the concentration of propionic acid is greater than or equal to about 10 μmol/g of cecal contents, and/or (2) the total volatile fatty acid concentration is approximately 100% or more greater than untreated controls.

Although propionic acid concentrations may be determined after the second day, the predictability of the efficacy decreases if based upon total volatile fatty acid concentration measurements made after the third day.

As with the above-mentioned 29 strain probiotic, steady state cultures produced in accordance with this process may be used directly as a probiotic, or stored for later use. Similarly, the bacteria comprising the culture may also be isolated and identified, and known or standard strains, or isolates form the same target animal, may be substituted for bacteria of the same genera or species in the steady state culture as described hereinabove.

Large quantities of the probiotics of this invention may be produced by either batch or continuous culture of the bacteria in a suitable culture medium using anaerobic culture techniques conventional in the art. Of these, continuous culture is of particular advantage, because the steady state cultures are exceedingly stable and may be maintained indefinitely under steady state culture. The inoculum for the large scale culture may be a sample or seed of the steady state culture, the deposit, or stock cultures or substantially biologically pure isolates of the bacteria. The bacteria may be cultured in combination, or in separate culture media and subsequently combined for ease of standardization. In accordance with the latter technique, the final concentration of each bacteria should be between about $10^8$ to $10^9$ organisms/ml prior to combination. However, the practitioner skilled in the art will recognize that the concentration is not critical and may vary.

Generally, when large scale production is conducted in batch culture, the culture should be incubated about 16–72 hours, preferably between about 24–48 hours, before harvesting. However, we have found that in any event, the batch culture should be continued until the following fermentation parameters are achieved:

(1) the concentration of acetic acid is greater than or equal to about 20 mM, (2) the concentration of propionic acid is greater than or equal to about 10 mM, (3) the concentration of butyric plus isobutyric acids is greater than or equal to about 15 mM.

The use of the probiotic of this invention is not affected by the particular method of production; probiotic produced by any of the above-described methods may be used in the same manner. Following production, the cultures of bacteria may be administered directly to the subject animal either singly or in combination. Optionally, the probiotic may be further formulated with a suitable carrier including, but not limited to lactose or skim milk, or combined with a small amount of feed for use as a premix. The cultures may also be freeze dried for storage stability and ease of handling. Such freeze dried culture may be directly administered to the animal or, in the alternative, reconstituted prior to use. Of special note, one or all of the bacteria may be encapsulated using techniques conventional in the art, including, but not limited to encapsulation in an alginate gel. Without wishing to be bound by theory, it is believed that encapsulation in this manner may prevent some bacteria from reducing the concentration of latic acid in the upper intestinal tract to undesirable levels, it may also protect the bacteria and allow them to reach the ceca, where lactic acid utilization is desirable.

The probiotic of this invention may also be combined with other substantially biologically pure bacteria which are used in probiotics effective for control of Salmonella in domestic animals or fowl and especially those bacteria producing lactic acid or volatile fatty acids. Without being limited thereto, other suitable bacteria include Peptostreptococcus species, or those described in DeLoach [U.S. patent application Ser. No. 07/822,505], the contents of which are incorporated by reference herein. Other adjuvants conventional or known in the art for the treatment of domestic animals and fowl, and particularly for the inhibition of enteropathogens, may be added to the probiotic. Suitable adjuvants include, for example, coccidiostats that are not effective against gram positive organisms. Addition of lactose is especially preferred.

Non-therapeutic levels of antibiotics may also be administered to the animal or fowl as is conventional in the art. Such antibiotics may be administered in combination with or apart form the probiotic. Alternatively, these antibiotics may be administered to fowl in ovo at levels which are therapeutical, but which decline to non-therapeutic levels within about 3 days after hatching.

While the probiotic of this invention is primarily administered or introduced to the alimentary tract by combining with the feed or water of the animal followed by oral ingestion thereof, it is envisioned that it may also be administered orally and nasally by spraying or misting the formulation directly upon the animal as is conventional in the art. Still other alternatives include injection directly into the gastrointestinal tract, or administration cloacally. In regard to the latter, the probiotic may be sprayed directly onto the vent of fowl or applied to the pen floor litter whereupon it will contact the vent area through the course of normal activity of the fowl. Once contacted with the vent area, the probiotic will be introduced into the cloaca by reverse peristalsis.

Administration of the probiotic may be at any time during the life of the animal. However, in the preferred embodiment the probiotic is administered to newly hatched fowl between about 1 to 14 days old.

The probiotic is administered in an amount effective to substantially inhibit the Salmonella colonization in the treated animal, in comparison with untreated animals. Suitable amounts may be readily determined by the practitioner skilled in the art, and will vary somewhat with the age and size of the animal.

The following examples are intended only to further illustrate the invention and are not intended to limit the scope of the subject matter which is defined by the claims.

EXAMPLE 1

Preparation of Probiotic

Initial Inoculum

The initial inoculum was obtained from three 10-week old salmonellae-free broiler chickens, reared from hatch on unmedicated feed and water. The birds were sacrificed and the ceca were removed aseptically and transferred immediately to an anaerobic chamber (Coy Laboratory Products, Ann Arbor, Mich.). Each cecum was cut into several pieces and macerated in a Lab Blender (Tekmar, Cincinnati, Ohio). The macerated cecal tissues and contents were combined and thoroughly homogenized and glycerol was added to a final concentration of 20%. The final cecal homogenate mixture was frozen at −70° C. until used. Ten ml of the frozen cecal homogenate were thawed and incubated anaerobically in 100 mL Viande Levure (VL) broth at 39° C. and used as a seed culture for the subsequent continuous-flow (CF) culture.

Continuous Flow Apparatus

Both the batch and continuous flow culture stages were conducted in an 1150 ml chemostat vessel of a BioFlo III fermenter (New Brunswick Scientific Co., Edison, N.J.). When the culture was grown under continuous flow conditions, the following parameters were used:

—dilution rate of $0.0416^{-1}$ (corresponding to a flow rate of 0.80 ml/minute and a vessel turnover time of 24 hr.),
—temperature of 39° C., and
—agitation rate of 200 rpm.

Anaerobic conditions were maintained by flushing the vessel with a constant stream of $O_2$-free $CO_2$.

Growth of Cecal Organisms Under Continuous Flow Conditions

The chemostat vessel was filled with 1,050 ml of sterile Viande Levure (VL) broth and inoculated with 100 ml of the seed culture and incubated anaerobically in batch culture at 39° C. with an agitation rate of 200 rpm. After 6 hours in batch culture, the nutrient pump was started and the culture was incubated under continuous-flow conditions. Steady state conditions were achieved after about 5 days of continuous-flow culture. Steady state conditions were assumed when culture pH, $OD_{600}$ and volatile fatty acid concentrations remained approximately constant.

Samples of the continuous-flow culture were collected aseptically after 5 days and 61 days of culture and plated on tryptose agar supplemented with 5% bovine blood, McConkey agar, and Center for Disease Control blood agar (CDCBA). The tryptose agar and McConkey agar plates were incubated in air at 37° C. for 7 days. The CDCBA plates were incubated in an anaerobic chamber (Coy Laboratory Products, Ann Arbor, Mich.) containing an atmosphere of 80% nitrogen, 10% hydrogen, and 10% carbon dioxide at 37° C. for 7 days. Twenty-nine bacterial isolates, composed of 15 facultative and 14 obligate anaerobes, representing 10 different genera, were identified in the 5 day and again in the 61 day continuous-flow culture. The 29 bacterial isolates were identified utilizing biochemical and enzymatic procedures and antimicrobial susceptibility profiles conventional in the art (Holdeman et al., 1977, Anaerobe Laboratory Manual, 4th ed., Virginia Polytechnic Institute and State University, Blacksburg, Va.; Farmer et al., 1985, J. Clin. Microbiol., 21:46–76; Lennette et al., 1985, Clinical Microbiology, 4th ed., American Society for Microbiology, Washington, D.C.; and Devriese et al., 1987, Int. J. Syst. Bacteriol., 37:257–259, the contents of each of which are incorporated by reference herein). The results are described in Example 2.

The bacteria were identified as:

I. Facultative anaerobic, gram positive cocci:
(1) *Enterococcus faecalis* designated strain M,
(2) *Enterococcus faecalis* designated strain N,
(3) *Enterococcus faecium* designated strain Y,
(4) *Enterococcus faecium* designated strain Z,
(5) *Enterococcus faecium* designated strain X,
(6) *Enterococcus avium*,
(7) *Enterococcus faecalis* designated strain O, II. Facultative anaerobic, gram-positive coccobacilli:
(8) *Lactococcus lactis* subspecies diacetylactis,
(9) a Lactobacillus species (strain no. 1), III. Facultative anaerobic, gram negative bacilli:
(10) *Escherichia coli* designated strain CC-3A,
(11) *Citrobacter freundii* strain designated CC-3,
(12) a bacterium belonging to the family Enterobacteriaceae (tentatively an Enterobacter species, *E. coli*, or *Kluyvera cryocrescens*),
(13) a Pseudomonas species,
(14) *Serratia liquefaciens*,
(15) *Escherichia coli* designated strain CC-3B, IV. Obligate anaerobic, gram positive bacilli:
(16) a Propionibacterium species (strain no. 1, tentatively *P. jensenii* or *P. thoenii*),
(17) a Propionibacterium species (strain no. 2, tentatively *P. granulosum*),
(18) a Lactobacillus species (strain no. 2),
(19) a Bifidobacterium species (strain no. 1) or a Lactobacillus species (strain no. 3),
(20) a Propionibacterium species (strain no. 3),
(21) a Eubacterium species (strain no. 1),
(22) a Eubacterium species (strain no. 2),
(23) an unknown bacterium designated strain OAGPB-5,
(24) a Bifidobacterium species (strain no. 3),
(25) a Bifidobacterium species (strain no. 2) or a Lactobacillus species (strain no. 4),
(26) a Bifidobacterium species (strain no. 3) or a Lactobacillus species (strain no. 4),
(27) a Propionibacterium species (strain no. 4), V. Obligate anaerobic, gram negative cocci:
(28) a Veillonella species, and VI. Obligate anaerobic, gram-negative bacilli:
(29) a Fusobacterium species.

The continuous-flow culture, thus characterized to be composed of 29 bacterial isolates, demonstrated compatible growth in mixed culture, viability in an acid environment (pH 5.0 to 6.5), and the production of volatile fatty acids (VFA) as fermentation end products.

The probiotic composition, including all 29 of the above-mentioned bacterial strains, has been deposited under the Budapest Treaty in the American Type Culture Collection (12301 Parklawn Drive, Rockville, Md. 20852, USA) as Competitive Exclusion Culture, CF3, and has been assigned Deposit No. ATCC 55515.

EXAMPLE 2

Characterization of Bacteria

Gas liquid chromatography

Each of the 29 bacterium strains from CDCBA was inoculated into peptone-yeast (PY) and PY+1% glucose (PYG) broths, then incubated anaerobically at 37° C. for 2 days. The volatile fatty acids (VFAs) and nonvolatile fatty acids (NVFAs) were extracted using a standard procedures, then detected with GowMac GLC. The GLC was calibrated with commercial VFAs and NVFAs standards. The results are shown in Tables 1A–C.

Cellular, colonial, and cultural characterization

The Gram reaction and cellular morphology of facultative anaerobic bacteria 1–15 were determined using Gram-stained smears from blood agar that had been incubated in air at 37° C. for 24 hours. The motility of the bacterium was determined using a soft agar (0.4%) motility medium with tetrazolium salts. The motility medium was inoculated from blood agar, then incubated in air at 37° C. for 24 hours. Each test was conducted twice.

To determine the culture characteristics, bacteria 1–9 were inoculated on 2 blood agar, 2 MacConkey agar, 2 sodium azide blood agar, and 2 bile esculin agar plates. One blood agar, 1 MacConkey agar, 1 sodium azide blood agar, and 1 bile esculin agar plates were incubated in air at 37° C. One blood agar and 1 MacConkey agar plates were incubated in an atmosphere of 80% nitrogen, 10% hydrogen, and 10% carbon dioxide at 37° C. One sodium azide blood agar and 1 bile esculin agar plates were incubated in air at 45° C. for 2 days. The ability to row, colonial characteristics and hemolytic pattern on blood agar, lactose reaction on MacConkey agar, and esculin hydrolysis reaction on bile esculin agar were recorded after 1 and 2 days incubation. Each test was conducted twice.

To determine the culture characteristics of facultative anaerobic gram-negative bacteria 10–15, the same procedure was repeated except the sodium azide blood agar and bile esculin agar plates were deleted.

For the obligate anaerobic bacteria 16–29, the gram reaction and cellular morphology of the bacterium were determined using Gram-stained smears from a brain heart infusion blood agar enriched with hemin and menadione (CDCBA) that had been incubated in an atmosphere of 80% nitrogen, 10% hydrogen, and 10% carbon dioxide at 37° C. for 2 days. The motility was determined using a commercial prereduced anaerobically sterilized (PRAS) medium from CDCBA, then incubated anaerobically at 37° C. for 2 days.

To determine the culture characteristics, bacteria 16–29 were inoculated on 2 CDCBA and 2 MacConkey agar plates. Once CDCBA and 1 MacConkey agar plates were incubated in air at 37° C., and 1 CDCBA and 1 MacConkey Agar plates were incubated anaerobically at 37° C. The ability to grown, and colonial characteristics and hemolytic pattern on CDCBA were recorded after 1, 3 and 5 days incubation. Each test was conducted twice.

The results are shown in Tables 2A–C.

Catalase, oxidase, and nitrate reduction tests

For the facultative anaerobic bacteria 1–9, colonies from blood agar that had been incubated in air at 37° C. for 2 days were used to conduct the catalase and oxidase tests. Reagents for the catalase test and oxidase test were 3% $H_2O_2$ and a 1% solution of tetramethyl-p-phenylenediamine dihydrochloride, respectively. The oxidase and catalase reactions were recorded as negative or positive. Each test was conducted twice. The same procedure was used for facultative anaerobic gram-negative bacteria 10–15 except that the cultures were only incubated 24 hours.

For the obligate anaerobic bacteria 16–29, colonies from CDCBA incubated anaerobically at 37° C. for 2 days were used to conduct the catalase and oxidase tests. Reagents for the catalase and oxidase test were the same as above. The bacteria for the catalase tests and oxidase test was exposed to air for 30 minutes prior to adding the reagents. All reactions were recorded as positive or negative. Each test was conducted twice.

Two methods were used to detect nitrate reductase in the facultative anaerobic bacteria 1–15. With the nitrate agar method, nitrate agar that contained a 0.1% $KNO_3$ was inoculated form blood agar that had been incubated in air at 37° C. for 24 hours. After 24 hours incubation at 37° C., reagents A and B (N,N-dimethyl-naphthylamine and sulfanilic acid) were applied. With the anaerobic blood agar-disk method, the organism was streaked on blood agar, then a paper disk impregnated with a 0.4% $KNO_3$ solution was placed on a heavily streaked area. The plate was incubated anaerobically at 37° C. for 24 hours, then reagents A and B were applied to the paper disk. To determine if nitrate was reduced beyond nitrate, zinc dust was added to the reagent treated disk. All reactions were recorded as negative or positive. Each test was conducted twice.

For the obligate anaerobic bacteria 16–29, nitrate reductase was determined using the anaerobic blood agar-disk method above, except that CDCBA was used rather than blood agar.

the results are shown in Tables 3A–C.

Aerobic carbohydrate utilization tests

For the facultative anaerobic bacteria 1–9, acid production from glucose, dulcitol, lactose, maltose, mannitol, salicin, and sucrose was determined using 1% substrate in a phenol red broth base. A Durham tube in the glucose broth was used to detect gas production. Each tube was inoculated with the test organism from blood agar that had been incubated in air at 37° C. for 24 hours. The broths were incubated in air at 37° C. for 2 days. Each tube was observed for a color change. Tubes with a red color were recorded as negative, and tubes with a yellow color were recorded as positive. Each test was conducted twice.

The same procedure was followed for the facultative anaerobic gram-negative bacteria 10–15 except that only glucose, lactose and sucrose were assayed.

Triple sugar iron (TSI) agar was inoculated from cultures of all facultative anaerobes 1–15 on blood agar that had been incubated in air at 37° C. for 24 hours. After 24 hours incubation in air at 37° C., the TSI agar reactions were recorded as positive or negative. The test was conducted twice.

For the facultative anaerobic bacteria 1–9, a Voges-Proskauer broth was inoculated form blood agar, then incubated in air at 37° C. for 24 hours. Reagents A and B (40% KOH and alpha-naphthol) were added, and the reaction was recorded as positive or negative. The test was conducted twice.

For the facultative anaerobic gram-negative bacteria 10–15, two methyl red-Voges Proskauer broth tubes (A and B) were incubated from a blood agar plate, then incubated in air at 37° C. for 24 hours. For the methyl red test, a solution of methyl red dye was added to tube A. For the Voges-Proskauer test, reagents A and B (405 KOH and alpha-naphthol) were added to tube B. The reactions were recorded as positive or negative. Each test was conducted twice.

The results are shown in Tables 3A–C.

Amino acid utilization and urease tests

The facultative anaerobic gram-negative bacteria 10–15 were assayed for lysine decarboxylase, and urease, and bacteria 1–15 were assayed for indole production. Lysine iron agar (LIA) was used to detect the lysine decarboxylase. LIA was inoculated from a blood agar plate, then incubated in air at 37° C. for 24 hours. The reactions were recorded as positive or negative. The tests were repeated twice.

Two methods were used to detect indole production from tryptophane. Tryptophane broth, which was inoculated from blood agar, was incubated in air at 37° C. for 24 hours, then reacted with Ehrlich's reagent. With the anaerobic agar-disk method, a blood agar plate was streaked with the organism, then a paper disk was placed on the agar surface. The blood agar plate was incubated anaerobically at 37° C. for 24 hours, then a 1% solution of p-dimethylaminocinnamaldehyde was applied to the disk. All results were recorded as positive or negative. The tryptophane broth test was repeated twice and the anaerobic agar-disk method once.

Urea agar was inoculated from a blood agar plate, then incubated in air at 37° C. for 24 hours. The reaction was recorded as positive or negative. The test was repeated twice.

These results are also shown in Tables 3A–C.

Commercial API 20E system

The facultative anaerobic gram-negative bacteria 10–15 were also evaluated for 20 biochemical reactions (Table 4) using a commercial system as described by the manufacturer (Analytab Products, Plainview, N.Y.). The tests were repeated twice.

The results are shown in Table 4.

Carbohydrate fermentation, gelatin liquefaction, and amino acid utilization tests.

Commercial prereduced anaerobically sterilized (PRAS) broth media (Table 5) were inoculated with a dense suspension of the facultative anaerobic bacteria 1–15 on blood agar. The broths were incubated in air at 37° C. for 5 days, and the pH of each culture was determined after 1, 3, and 5 days incubation with a pH meter. Cultures with a pH of $\leq 6.5$ were recorded as positive, and cultures with a pH of $\geq 6.6$ as negative. Arginine media was evaluated for an increased pH, while the gelatin media was evaluated for liquefaction. Each test was conducted once.

The same procedure was reported with obligate anaerobic bacteria 16–29 except the inoculum was prepared from organisms grown on CDCBA and all incubations were anaerobic.

The results are shown in Tables 4A–C and 3A–C.

Commercial API Rapid STREP system tests

Facultative anaerobic bacteria 1–9 were evaluated for 20 biochemical properties (Table 6) using a commercial system for the identification of enterococci and streptococci as described by the manufacturer (Analytab Products, Plainview, N.Y.). Briefly, colonies from blood agar that had been incubated in air at 37° C. for 24 hours were suspended in 3 ml of sterile distilled water to provide a bacterial suspension equivalent to a McFarland number 5 standard. Each cupule was inoculated, and the strips were incubated in air at 37° C. for 24 hours. After 24 hours of incubation, reagents were added to test for acetoin production, hippurate hydrolysis, and enzymatic reactions for pyrrolidonyl-2-naphthylamide, alpha-galactosidase, beta-glucuronidase, beta-galactosidase, alkaline phophatase, and leucine arylamidase. Reactions were recorded after 10 minutes incubation at room temperature as either positive or negative. The esculin hydrolysis, arginine dihydrolase, and acid production from ribose, arabinose, mannitol, sorbitol, lactose, trehalose, inulin, raffinose, starch, and glycogen were recorded as either positive or negative. Each test was conducted twice.

The results are shown in Table 6.

Commercial API STAPH Trac System tests

Facultative anaerobic bacteria 1–9 were evaluated for 19 biochemical properties (Table 7) using a commercial system as described by the manufacturer (Analytab Products, Plainview, N.Y.). Briefly, colonies from blood agar that had been incubated in air at 37° C. for 24 hours were suspended in 3 ml of sterile distilled water to provide a bacterial suspension equivalent to a McFarland number 5 standard. Each cupule was inoculated, and the strips were incubated in air at 37° C. for 24 hours. After 24 hours incubation, reagents were added to test for acetoin production, alkaline phosphatase, nitrate reductase, and enzymatic reactions for alpha-methyl-glucoside, arginine dihydrolase, glucose, fructose, maltose, mannitol, mannose, melibiose, N-acetyl-glucosamine, raffinose, saccarose, trehalose, urease, xylitol, and xylose. Reactions were recorded as positive or negative. Each test was conducted twice.

The results are shown in Table 7.

Commercial API ZYM system tests

All facultative anaerobic bacteria 1–15 were evaluated for enzyme activities of 19 substrates (Table 8) using a commercial semiquantitative enzyme system as described by the manufacturer (Analytab Products, Plainview, N.Y.) Briefly, colonies form blood agar that had been incubated in air at 37° C. for 24 hours were suspended in 3 ml of sterile distilled water to provide a bacterial suspension equivalent to a McFarland number 5 standard. Each cupule of the strip was inoculated with the bacterial suspension. After incubation at 37° C. for 4 hours in the dark, reagents A and B were added to each cupule, and the reactions were allowed to develop for 5 minutes at room temperature. The color intensities of the reactions were compared to the manufacturer's interpretation scheme and graded as follows: 0=no color change, trace =<5 nanomoles (nmol), 1=5 nmol, 2=10 nmol, 3=20 nmol, 4=30 nmol, and 5≧40 nmol.

The same procedure was repeated with obligate anaerobic bacteria 16–29 except that the inoculum was prepared from organisms grown anaerobically on CDCBA.

The results are shown in Tables 8A–C.

Commercial Presumpto Plates I, II, and III

For obligate anaerobic bacteria 16–29, Presumpto plates I, II, and III were inoculated from CDCBA, then incubated anaerobically at 37° C. for 2 days. The tests were conducted and results recorded as described by the manufacturer (Table 9). Each test was conducted twice.

The results are shown in Tables 9A–D.

Antimicrobial Susceptibility Tests

The standard disk-diffusion procedure was used to test facultative anaerobic bacteria 1–15 for their antimicrobial susceptibility to selected antimicrobial agents as shown in Table 10. The results were recorded as resistant or susceptible (including moderately susceptible). Each test was conducted once.

The same procedure was repeated with obligate anaerobic bacteria 16–19 except that CDCBA was used and the cultures were incubated anaerobically.

The results are shown in Tables 10A–C.

Results

The results of the profiles are shown in Tables 1 to 10. All bacteria were identified according to standard culture and biochemical criteria.

EXAMPLE 3

In Vivo Experiments With Broiler Chicks

Salmonella

A primary poultry isolate of *S. typhimurium* obtained from the National Veterinary Services Laboratory, Ames, IA 50010 was selected for resistance to novobiocin (NO) and nalidixic acid (NA) in our laboratory and maintained in media containing 25 µg NO and 20 µg NA/mL. Challenge inocula were prepared from an overnight culture that had previously been transferred three times in trypticase soy broth and serially diluted in sterile phosphate-buffered saline to a concentration of $4 \times 10^4$ cfu/1.0 mL. The viable cell concentration of the challenge inoculum was confirmed by colony counts on brilliant green agar (BGA) plates. Media used to culture the NO-NA resistance isolate form challenged chicks in experimental studies contained 25 µg NO and 20 µg NA/mL to inhibit the growth of other bacteria and nonresistant salmonellae.

Experimental Design

Male broiler chicks were obtained on the day of hatch from a commercial hatchery and placed in floor pens on pine shaving litter. The chicks were maintained under continuous lighting and provided free access to water and an unmedicated corn and soybean meal diet that contained or exceeded the levels of critical nutrients recommended by the National Research Council (1984). The paper liners form the chick transport boxes and three randomly selected 25 g samples of the feed ration were cultured successively in buffered peptone water, selenite cystine broth, and on BGA plates as described previously (Andrews et al., 1978, Isolation and Identification of Salmonella, In: Bacteriological Analytical Manual, 5th ed., Assoc. Off. Anal. Chem., Washington, D.C., Chapter 6, 1–24) and examined for salmonellae. Salmonella spp. were not detected in the paper liners or feed ration. The chicks were randomly assigned to two groups and provided either 1) no treatment (controls) or 2) characterized culture (CC) in their first drinking water. The CC was collected as effluent from the continuous-flow culture of Example 1, contained approximately $10^8$ anaerobic cfu/mL, and was added to the drinking water at a 1.5 ratio (1 part CC; 4 parts water). The treated chicks were provided treated water for 18 h and each chick was estimated to have drank 10 mL of the CC treated water. After 18 h, the remaining treated water was removed and replaced with fresh tap water. On day three, two days after CC treatment and prior to Salmonella challenge, 10 chicks in each group were randomly selected and euthanatized by cervical dislocation. The concentration of propionic volatile fatty acid (VFA) and total VFA concentrations (acetic+ propionic+butyric+isobutyric+valeric+ isovaleric) in the cecal contents were determined by gas liquid chromatography as reported previously (Corrier et al., 1990, Avian Dis., 34:617–625). All remaining chicks were challenged by crop gavage at 3 days of age with $10^4$ cfu S. typhimurium as recommended for evaluating the efficacy of newly prepared cultures of cecal bacteria (mead et al., 1989, J. Food Protect., 52:500–502). At 10 days of age, 20 chicks in each group were euthanatized and cecal contents from each chick were collected aseptically and evaluated for S. typhimurium colonization as described hereinbelow. The cecal contents form 10 of the 10 day old euthanatized chicks were selected randomly and VFA concentration determined as described above. The experimental design was repeated in four separate trials using newly hatched chicks and characterized cecal bacteria maintained in continuous-flow culture for 5 days (Trial 1), 26 days (Trial 2), 40 days (Trial 3), and 61 days (Trial 4). The concentrations of VFA's in the cecal contents were determined during Trials 2, 3, and 4 but not during Trial 1.

The concentration of propionic acid in the cecal contents of the treated chicks was elevated significantly ($P<0.005$) compared with the controls on day 3 and on day 10 in Trials 2, 3, and 4 (Table 11). Additionally, a significant correlation ($P<0.005$) occurred between the increased concentrations of the cecal propionic acid in the 3-day old treated chicks and the $\log_{10}$ decrease in the number of Salmonella in the cecal contents of the 10-day old treated chicks ($r=-0.99$.)

On day 3, the concentration of total VFA's in the cecal contents of the treated chicks was elevated significantly ($P<0.01$) compared with the control chicks (Table 12). Additionally, a significant correlation ($PP<0.01$) occurred between the increased concentration of total VFA in the 3-day old treated chicks and the $\log_{10}$ decrease in the number of Salmonella in the cecal contents of the 10-day old treated chicks ($r=-0.67$). On day 10, the concentration of total VFA's in the ceca of the treated chicks was significantly elevated ($P<0.05$) compared to the control chicks in the Trials 3 and 4.

Cecal colonization by S. typhimurium

As mentioned above, one cecum from each chick was removed aseptically, minced with scissors, and incubated in 30 mL of selenite-cystine broth for 24 h at 37° C. After incubation, the broth was streaked on BGA plates, incubated for 24 h and examined for typical S. typhimurium colonies. A portion (0.2 g) of the contents from the remaining cecum were serially diluted and spread-plated on BGA plates at dilutions of 1:100, 1:1000, and 1:10,000. The plates were incubated for 24 h at 37° C. and the number of cfu of S. typhimurium was determined using an automatic colony counter (Biotran III, New Brunswick Scientific, Edison, N.J.). Typical Salmonella colonies were confirmed by biochemical tests on triple sugar iron agar and lysine iron agar (Difco laboratories, Detroit, Mich.) and further identified as S. typhimurium serologically using Salmonella O Antiserium, Group 13, Factors 1, 4, 12, 15 (Difco Laboratories, Detroit, Mich.). Salmonella colony plate counts were expressed as $\log_{10}$ Salmonella per gram of cecal contents. Cecal contents that were Salmonella-culture-negative at the 1:100 dilution but positive after culture in selenite-cystine were arbitrarily assigned a value of 1.50 $\log_{10}$ Salmonella/g cecal contents. Selenite cystine cultures that were negative on BGA plates were assigned a $\log_{10}$ Salmonella value of 0.

To evaluate the efficacy of CC treatment on resistance to Salmonella challenge, the "protection factor" (PF) was calculated as described previously (Pivnick and Nurmi, 1982, The Nurmi Concept and its Role in the Control of Salmonellae in Poultry, In: Developments in Food Microbiology, Davies (ed.), Applied Sciences Publishers, London, 41–70; Mead et al., 1989, J. Food Protect., 52:500–502). The PF=(mean $\log_{10}$ Salmonella control group/mean $\log_{10}$ Salmonella treated group).

Differences in the number of S. typhimurium culture-positive chicks between groups were analyzed by chi-square analysis. Differences between means were determined using Student's t test. Significance of correlation and all statistical procedures were performed as described (Snedecor and Cochran, 1967, Statistical Methods, 6th ed., Iowa State University Press, Ames, Ia.).

Compared to controls, the number of S. typhimurium in the cecal contents of the treated chicks decreased significantly ($P< 0.005$) by 6/35, 5.39, 3.84, and 5.77 $\log_{10}$ units in each of Trials 1, 2, 3 and 4, respectively (Table 13). The protection factor, calculated to assess the efficacy of the characterized culture, was determined to be 63.5, 7.14, 15.2, and 10.6 for Trials 1, 2, 3 and 4, respectively.

The experimental challenge dose of $10^4$ S. typhimurium resulted in cecal colonization in 90% to 100% of the control chicks at 10-days of age during the four trials (Table 6). Compared to controls, the number of Salmonella cecal culture-positive chicks in the treated group decreased significantly ($P<0.01$) by 100%, 65%, 75%, and 60% in each of Trials 1, 2, 3, and 4, respectively.

EXAMPLE 4

Preparation of Probiotic

A second steady state culture was prepared using the continuous culture process of this invention, as described in U.S. patent application Ser. No. 07/921,173, filed Jul. 29, 1992, the contents of which are incorporated by reference herein.

The steady state culture, designated CFII, consisted of eleven different bacteria, including four facultative anaerobic gram-positive cocci, two facultative anaerobic gram-positive bacilli, three facultative anaerobic gram-negative bacilli, one obiligate anaerobic gram-positive bacillus, and one obiligate anaerobic gram-positive coccobacillus. The bacteria were identified as:

(1) *Enterococcus faecalis* (designated strain A),
(2) *Enterococcus faecalis* (designated strain B),
(3) *Enterococcus avium*,
(4) *Lactococcus lactis*,
(5) Lactobacillus species (designated CMS),
(6) *Lactobacillus animalis*,
(7) *Citrobacter freundii*,
(8) *Escherichia coli*,
(9) *Escherichia fergusonii*,
(10) *Bifidobacterium animalis*, and
(11) *Propionibacterium acidipropionici*.

The steady state culture demonstrated substantial effectiveness as a probiotic when administered to fowl, significantly decreasing the colonization of fowl by *Salmonella typhimurium* and *S. enteritidis* in comparison to untreated birds.

It is understood that the foregoing detailed description is given merely by way of illustration and that modifications and variation may be made therein without departing form the spirit and scope of the invention.

TABLE 1A

|  | Group I | | | | | | | Group 2 | |
| --- | --- | --- | --- | --- | --- | --- | --- | --- | --- |
|  | 1 PY/PG | 2 PY/PG | 3 PY/PG | 4 PY/PG | 5 PY/PG | 6 PY/PG | 7 PY/PG | 8 PY/PG | 9 PY/PG |
| VFAs | | | | | | | | | |
| Formic | S/S | S/S | —/— | T/— | —/— | —/— | —/T | —/— | —/— |
| Acetic | S/S | S/S | T/T | T/— | —/T | —/— | S/T | —/— | T/T |
| Propionic | —/— | —/— | —/— | —/— | —/— | —/— | —/— | —/— | —/— |
| Isobutyric | —/— | —/— | —/— | —/— | —/— | —/— | —/— | —/— | —/— |
| Butyric | —/— | —/— | —/— | —/— | —/— | —/— | —/— | —/— | —/— |
| Isovaleric | —/— | —/— | —/— | —/— | —/— | —/— | —/— | —/— | —/— |
| Valeric | —/— | —/— | —/— | —/— | —/— | —/— | —/— | —/— | —/— |
| Isocaproic | —/— | —/— | —/— | —/— | —/— | —/— | —/— | —/— | —/— |
| Caproic | —/— | —/— | —/— | —/— | —/— | —/— | —/— | —/— | —/— |
| NVFAs | | | | | | | | | |
| Pyruvic | —/— | —/— | —/— | —/— | —/— | —/— | —/— | —/— | —/— |
| Lactic | T/L | T/L | T/L | S/L | T/L | T/L | L/L | S/L | T/L |
| Oxalacetic | —/— | —/— | —/— | —/— | —/— | —/— | —/— | —/— | —/— |
| Malonic | —/— | —/— | —/— | —/— | —/— | —/— | —/— | —/— | —/— |
| Fumaric | —/— | —/— | —/— | —/— | —/— | —/— | —/— | —/— | —/— |
| Succinic | —/— | —/— | —/— | —/— | —/— | —/— | —/— | —/— | —/— |
| Benzoic | —/— | —/— | —/— | —/— | —/— | —/— | —/— | —/— | —/— |
| Phenylacetic | —/— | —/— | —/— | —/— | —/— | —/— | —/— | —/— | —/— |

The amounts of VFAs and NVGAs are expressed as follows: — = none produced; T = trace amounts produced; S = small amounts produced; L = large amounts produced; and V = very large amounts produced

TABLE 1B

|  | Group III | | | | | | Group IV | | | | |
| --- | --- | --- | --- | --- | --- | --- | --- | --- | --- | --- | --- |
|  | 10 PY/PG | 11 PY/PG | 12 PY/PG | 13 PY/PG | 14 PY/PG | 15 PY/PG | 16 PY/PG | 17 PY/PG | 18 PY/PG | 19 PY/PG | 20 PY/PG |
| VFAs | | | | | | | | | | | |
| Formic | —/— | —/— | —/— | —/— | —/— | —/— | —/T | —/— | —/— | —/— | —/— |
| Acetic | S/L | S/S | S/L | T/T | T/— | S/S | T/S | S/S | T/T | —/— | S/S |
| Propionic | T/— | T/— | T/— | —/— | —/— | —/— | T/L | L/L | —/— | —/— | S/S |
| Isobutyric | —/— | —/— | —/— | —/— | —/— | —/— | —/— | —/— | —/— | —/— | —/— |
| Butyric | —/— | —/— | —/— | —/— | —/— | —/— | —/— | —/— | —/— | —/— | —/— |
| Isovaleric | —/— | —/— | —/— | —/— | —/— | —/— | —/— | —/— | —/— | —/— | —/— |
| Valeric | —/— | —/— | —/— | —/— | —/— | —/— | —/— | —/— | —/— | —/— | /— |
| Isocaproic | —/— | —/— | —/— | —/— | —/— | —/— | —/— | —/— | —/— | —/— | —/— |
| Caproic | —/— | —/— | —/— | —/— | —/— | —/— | —/— | —/— | —/— | —/— | —/— |
| NVFAs | | | | | | | | | | | |
| Pyruvic | —/— | —/— | —/— | —/— | —/— | —/— | —/— | —/— | —/— | —/— | —/— |
| Lactic | —/L | —/L | —/L | —/— | —/S | L/— | T/S | T/S | S/S | —/— | —/— |
| Oxalacetic | —/— | —/— | —/— | —/— | —/— | —/— | —/— | —/— | —/— | —/— | —/— |
| Malonic | —/— | —/— | —/— | —/— | —/— | —/— | —/— | —/— | —/— | —/— | —/— |
| Fumaric | —/— | —/— | —/— | —/— | —/— | —/— | —/— | —/— | —/— | —/— | —/— |
| Succinic | —/— | —/— | —/— | —/— | —/T | —/— | —/— | —/— | —/— | —/— | S/S |

TABLE 1B-continued

|  | Group III | | | | | | Group IV | | | | |
| --- | --- | --- | --- | --- | --- | --- | --- | --- | --- | --- | --- |
|  | 10 PY/PG | 11 PY/PG | 12 PY/PG | 13 PY/PG | 14 PY/PG | 15 PY/PG | 16 PY/PG | 17 PY/PG | 18 PY/PG | 19 PY/PG | 20 PY/PG |
| Benzoic | L/L | L/T | L/T | —/— | —/— | L/L | T/T | —/— | —/— | —/— | —/— |
| Phenylacetic | —/— | —/— | —/— | —/— | —/— | —/— | —/— | —/— | —/— | —/— | —/— |

TABLE 1C

|  | Group IV | | | | | | | Group V | Group VI |
| --- | --- | --- | --- | --- | --- | --- | --- | --- | --- |
|  | 21 PY/PG | 22 PY/PG | 23 PY/PG | 24 PY/PG | 25 PY/PG | 26 PY/PG | 27 PY/PG | 28 PY/PG | 29 PY/PG |
| VFAs | | | | | | | | | |
| Formic | —/— | —/— | —/— | T/— | —/— | —/— | —/— | —/— | —/— |
| Acetic | S/L | L/S | S/— | S/— | —/— | —/S | T/T | T/T | S/T |
| Propionic | —/— | —/— | —/— | S/L | —/— | —/— | S/— | L/L | —/— |
| Isobutyric | —/— | —/— | —/— | —/T | —/— | —/— | —/— | —/— | —/— |
| Butyric | V/L | —/S | —/— | —/S | —/— | —/— | —/— | —/— | L/V |
| Isovaleric | —/— | —/— | —/— | —/L | —/— | —/— | —/— | —/— | —/— |
| Valeric | —/— | —/— | —/— | —/— | —/— | —/— | —/— | —/— | —/— |
| Isocaproic | —/— | —/— | —/— | —/— | —/— | —/— | —/— | —/— | —/— |
| Caproic | —/— | —/— | —/— | —/— | —/— | —/— | —/— | —/— | —/— |
| NVFAs | | | | | | | | | |
| Pyruvic | —/— | —/— | —/— | —/— | —/— | —/— | —/— | —/— | —/— |
| Lactic | T/S | T/— | —/— | —/— | S/L | T/L | —/— | —/— | —/— |
| Oxalacetic | —/— | —/— | —/— | —/— | —/— | —/— | —/— | —/— | —/— |
| Malonic | —/— | —/— | —/— | —/— | —/— | —/— | —/— | —/— | —/— |
| Fumaric | —/— | —/— | —/— | —/— | —/— | —/— | —/— | —/— | —/— |
| Succinic | —/— | —/— | —/— | —/— | —/— | —/— | —/— | —/— | —/— |
| Benzoic | S/— | —/L | L/— | L/— | —/— | —/— | L/L | —/— | —/— |
| Phenylacetic | —/— | —/— | —/— | —/— | —/— | —/— | —/— | —/— | —/— |

TABLE 2A

| | Cellular, Cultural and Colonial Characteristics | | | | | | | | | |
| --- | --- | --- | --- | --- | --- | --- | --- | --- | --- | --- |
| Condition | 1 | 2 | 3 | 4 | 5 | 6 | 7 | 8 | 9 | 10 |
| Gram Reaction | + | + | + | + | + | + | + | + | + | − |
| Morphology | c | c | c | c | c | c | c | cb | b | b |
| Motility | − | − | − | − | − | − | − | − | − | − |
| Respiration | fa | fa | fa | fa | fa | fa | fa | fa | fa | fa |
| Growth on: | | | | | | | | | | |
| Blood Agar | + | + | + | + | + | + | + | + | + | + |
| MacConkey Agar | − | − | − | − | − | − | − | − | − | + |
| Sodium Azide Blood Agar | + | + | + | + | + | + | + | − | − | NA |
| Bile Esculin Agar (37 C.) | + | + | + | + | + | + | + |  |  | NA |
| Bile Esculin Agar (45 C.) | + | + | + | + | + | + | + |  |  | NA |
| CDCBA | NA | NA | NA | NA | NA | NA | NA | NA | NA | NA |
| Hemolysis | − | − | + | + | + | + | − | + | + | − |
| Lactose Reaction on MacConkey Agar | NA | NA | NA | NA | NA | NA | NA | NA | NA | + |
| Esculin Hydrolysis | + | + | + | + | + | + | + |  |  | NA |

Morphology: c = *coccus*, b = *bacillus*, cb = *coccobacillus*
Respiration: oa = obligate anaerobe, fa = facultative anaerobe
CDCBA = Brain heart infusion blood agar enriched with hemin and menadione
hemolysis determined on Blood agar for facultative and on CDCBA for obligate anaerobes
NA = not applicable

TABLE 2B

Cellular, Cultural and Colonial Characteristics

| Condition | 11 | 12 | 13 | 14 | 15 | 16 | 17 | 18 | 19 | 20 |
|---|---|---|---|---|---|---|---|---|---|---|
| Gram Reaction | − | − | − | − | − | + | + | + | + | + |
| Morphology | b | b | b | b | b | b | b | b | b | b |
| Motility | + | − | + | + | − | − | − | − | − | − |
| Respiration | fa | fa | fa | fa | fa | oa | oa | oa | oa | oa |
| Growth on: | | | | | | | | | | |
| Blood Agar | + | + | + | + | + | NA | NA | NA | NA | NA |
| MacConkey Agar | + | + | + | + | + | − | − | − | − | − |
| Sodium Azide Blood Agar | NA | NA | NA | NA | NA | NA | NA | NA | NA | NA |
| Bile Esculin Agar (37 C.) | NA | NA | NA | NA | NA | NA | NA | NA | NA | NA |
| Bile Esculin Agar (45 C.) | NA | NA | NA | NA | NA | NA | NA | NA | NA | NA |
| CDCBA | NA | NA | NA | NA | NA | + | + | + | + | + |
| Hemolysis | − | − | − | − | − | − | − | + | − | − |
| Lactose Reaction on MacConkey Agar | + | + | − | − | + | | | | | |
| Esculin Hydrolysis | NA | NA | NA | NA | NA | NA | NA | NA | NA | NA |

TABLE 2C

Cellular, Cultural and Colonial Characteristics

| Condition | 21 | 22 | 23 | 24 | 25 | 26 | 27 | 28 | 29 |
|---|---|---|---|---|---|---|---|---|---|
| Gram Reaction | + | + | + | + | + | + | + | − | − |
| Morphology | b | cb | b | b | b | b | cb | c | b |
| Motility | − | − | − | − | − | − | − | − | − |
| Respiration | oa | oa | oa | oa | oa | oa | oa | oa | oa |
| Growth on: | | | | | | | | | |
| Blood Agar | NA | NA | NA | NA | NA | NA | NA | NA | NA |
| MacConkey Agar | − | − | − | − | − | − | − | − | − |
| Sodium Azide Blood Agar | NA | NA | NA | NA | NA | NA | NA | NA | NA |
| Bile Esculin Agar (37 C.) | NA | NA | NA | NA | NA | NA | NA | NA | NA |
| Bile Esculin Agar (45 C.) | NA | NA | NA | NA | NA | NA | NA | NA | NA |
| CDCBA | + | + | + | + | + | + | + | + | + |
| Hemolysis | | | | | | | | − | − |
| Lactose Reaction on MacConkey Agar | | | | | | | | | |
| Esculin Hydrolysis | NA | NA | NA | NA | NA | NA | NA | NA | NA |

TABLE 3A

Biochemical Characteristics

| Condition | 1 | 2 | 3 | 4 | 5 | 6 | 7 | 8 | 9 | 10 |
|---|---|---|---|---|---|---|---|---|---|---|
| Catalase | − | − | − | − | − | − | − | − | − | + |
| Oxidase | − | − | − | − | − | − | − | − | − | − |
| Nitrate Reduction: | | | | | | | | | | |
| Nitrate agar | − | − | − | − | − | − | − | − | − | + |
| Anaerobic | − | − | − | − | − | − | − | − | + | + |
| Glucose Broth | | | | | | | | | | |
| Acid | + | + | + | + | + | + | + | + | + | + |
| Gas | − | − | − | − | − | − | − | − | − | + |
| Carbohydrate Utilization | | | | | | | | | | |
| Dulcitol | − | − | − | − | − | − | − | − | − | |
| Lactose | + | + | + | + | + | + | + | + | + | + |
| Maltose | + | + | + | + | + | + | + | + | + | |
| Mannitol | + | + | + | + | + | + | + | + | + | − |
| Salicin | + | + | + | + | + | + | + | + | + | |
| Sucrose | + | + | + | + | + | + | + | + | + | + |
| TSI Agar | | | | | | | | | | |
| Butt/Slant | a/a | a/a | a/a | a/a | a/a | a/a | a/a | a/a | a/a | a/a |
| Gas | − | − | − | − | − | − | − | − | − | + |

TABLE 3A-continued

| Condition | Biochemical Characteristics | | | | | | | | | |
|---|---|---|---|---|---|---|---|---|---|---|
| | 1 | 2 | 3 | 4 | 5 | 6 | 7 | 8 | 9 | 10 |
| Hydrogen Sulfide | − | − | − | − | − | − | − | − | − | − |
| Methyl Red | + | + | + | + | + | + | + | | − | + |
| Vogues-Proskauer | − | − | − | − | − | − | − | + | − | − |
| Indole Production | − | − | − | − | − | − | − | − | − | + |
| Citrate | + | + | − | + | − | − | − | − | − | − |
| Malonate | − | − | − | − | − | − | − | − | − | − |
| Arginine Dihydrolase | + | + | + | + | − | + | + | + | + | |
| Lysine Decarboxylase | NA | NA | NA | NA | NA | NA | NA | NA | NA | + |
| Gelatin Liquefaction | + | + | − | − | − | − | − | − | − | |
| Urease | − | − | − | − | − | − | − | − | − | − |

Nitrate reduction:
Nitrate agar: + = growth, − = no growth
Anaerobic: determined by blood agar disk method
Carbohydrate utilization: + = acid produced, − = no acid produced
TSI agar butt/slant: a = acid, b = alkaline,
Lysine decarboxylase determined for LIA agar
NA = not applicable

TABLE 3B

| Condition | Biochemical Characteristics | | | | | | | | | |
|---|---|---|---|---|---|---|---|---|---|---|
| | 11 | 12 | 13 | 14 | 15 | 16 | 17 | 18 | 19 | 20 |
| Catalase | + | + | + | + | + | − | − | − | − | − |
| Oxidase | − | − | + | − | − | − | − | − | − | − |
| Nitrate Reduction: | | | | | | | | | | |
| Nitrate agar | + | + | + | + | + | NA | NA | NA | NA | NA |
| Anaerobic | + | + | + | + | + | − | − | − | | |
| Glucose Broth | | | | | | | | | | |
| Acid | + | | − | + | + | NA | NA | NA | NA | NA |
| Gas | + | | − | − | + | NA | NA | NA | NA | NA |
| Carbohydrate Utilization | | | | | | | | | | |
| Dulcitol | | | − | − | − | NA | NA | NA | NA | NA |
| Lactose | + | + | − | − | + | NA | NA | NA | NA | NA |
| Maltose | | | − | + | + | NA | NA | NA | NA | NA |
| Mannitol | | | − | + | | NA | NA | NA | NA | NA |
| Salicin | | | − | | | NA | NA | NA | NA | NA |
| Sucrose | + | + | − | + | − | NA | NA | NA | NA | NA |
| TSI Agar | | | | | | | | | | |
| Butt/Slant | a/a | a/a | b/b | a/b | a/a | NA | NA | NA | NA | NA |
| Gas | + | + | − | | + | NA | NA | NA | NA | NA |
| Hydrogen Sulfide | + | − | − | | − | NA | NA | NA | NA | NA |
| Methyl Red | + | + | − | + | + | NA | NA | NA | NA | NA |
| Vogues-Proskauer | − | − | − | − | − | NA | NA | NA | NA | NA |
| Indole Production | − | + | − | − | + | NA | NA | NA | NA | NA |
| Citrate | + | − | + | + | + | NA | NA | NA | NA | NA |
| Malonate | + | + | | | | NA | NA | NA | NA | NA |
| Arginine Dihydrolase | | | | | | − | − | + | + | − |
| Lysine Decarboxylase | − | + | + | + | + | | | | | |
| Gelatin Liquefaction | | | | | | − | − | − | − | − |
| Urease | − | − | − | − | − | − | − | − | − | − |

TABLE 3C

| Condition | Biochemical Characteristics | | | | | | | | |
|---|---|---|---|---|---|---|---|---|---|
| | 21 | 22 | 23 | 24 | 25 | 26 | 27 | 28 | 29 |
| Catalase | − | − | − | − | − | − | − | − | − |
| Oxidase | − | − | − | − | − | − | − | − | − |

TABLE 3C-continued

| | Biochemical Characteristics | | | | | | | | |
|---|---|---|---|---|---|---|---|---|---|
| Condition | 21 | 22 | 23 | 24 | 25 | 26 | 27 | 28 | 29 |
| Nitrate Reduction: | | | | | | | | | |
| Nitrate agar | NA | NA | NA | NA | NA | NA | NA | NA | NA |
| Anaerobic | | | | | | | | − | |
| Glucose Broth | | | | | | | | | |
| Acid | NA | NA | NA | NA | NA | NA | NA | NA | NA |
| Gas | NA | NA | NA | NA | NA | NA | NA | NA | NA |
| Carbohydrate Utilization | | | | | | | | | |
| Dulcitol | NA | NA | NA | NA | NA | NA | NA | NA | NA |
| Lactose | NA | NA | NA | NA | NA | NA | NA | NA | NA |
| Maltose | NA | NA | NA | NA | NA | NA | NA | NA | NA |
| Mannitol | NA | NA | NA | NA | NA | NA | NA | NA | NA |
| Salicin | NA | NA | NA | NA | NA | NA | NA | NA | NA |
| Sucrose | NA | NA | NA | NA | NA | NA | NA | NA | NA |
| TSI Agar | | | | | | | | | |
| Butt/Slant | NA | NA | NA | NA | NA | NA | NA | NA | NA |
| Gas | NA | NA | NA | NA | NA | NA | NA | NA | NA |
| Hydrogen Sulfide | NA | NA | NA | NA | NA | NA | NA | NA | NA |
| Methyl Red | NA | NA | NA | NA | NA | NA | NA | NA | NA |
| Vogues-Proskauer | NA | NA | NA | NA | NA | NA | NA | NA | NA |
| Indole Production | NA | NA | NA | NA | NA | NA | NA | NA | NA |
| Citrate | NA | NA | NA | NA | NA | NA | NA | NA | NA |
| Malonate | NA | NA | NA | NA | NA | NA | NA | NA | NA |
| Arginine Dihydrolase | | | | + | + | − | − | + | + |
| Lysine Decarboxylase | | | | | | | | | |
| Gelatin Liquefaction | | | | − | − | − | − | − | − |
| Urease | | | | − | − | − | − | − | + |

TABLE 4

API 20E System

| | Bacterium (isolate) | | | | | |
|---|---|---|---|---|---|---|
| Biochemical Tests | 10 | 11 | 12 | 13 | 14 | 15 |
| ONPG | +/+ | +/+ | +/+ | −/− | +/+ | +/+ |
| Arginine Dihydrolase | −/− | +/+ | −/− | +/+ | +/+ | −/− |
| Lysine Decarboxylase | +/+ | −/− | +/+ | +/+ | +/+ | +/+ |
| Ornithine Decarboxylase | +/+ | −/− | +/+ | +/+ | +/+ | −/− |
| Citrate | −/− | +/+ | −/− | +/+ | +/+ | −/− |
| H$_2$S | −/− | +/+ | −/− | −/− | −/− | −/− |
| Urease | −/− | −/− | −/− | +/+ | +/+ | −/− |
| Typtophane Deaminase | −/− | −/− | −/− | −/− | −/− | −/− |
| Indole | +/+ | −/− | +/+ | −/− | −/− | +/+ |
| Voges-Proskauer | −/− | −/− | −/− | −/− | +/+ | −/− |
| Gelatin | −/− | −/− | −/− | +/+ | +/+ | −/− |
| Glucose | +/+ | +/+ | +/+ | −/− | +/+ | +/+ |
| Mannitol | +/+ | +/+ | +/+ | −/− | +/+ | +/+ |
| Inositol | −/− | −/− | −/− | −/− | +/+ | −/− |
| Sorbitol | +/+ | +/+ | +/+ | −/− | +/+ | +/+ |
| Rhamnose | +/+ | +/+ | +/+ | −/− | +/+ | +/+ |
| Sucrose | +/+ | −/− | +/+ | −/− | +/+ | +/+ |
| Melibiose | +/+ | −/− | +/+ | −/− | +/+ | +/+ |
| Amygdalin | −/− | −/− | +/+ | −/− | +/+ | −/− |
| Arabinose | +/+ | +/+ | +/+ | −/− | +/+ | +/+ |

*Data of replicate 1/replicate 2

TABLE 5A

Carbohydrate Fermentation Tests

| | Bacterium (isolate) | | | | | | | | | | |
|---|---|---|---|---|---|---|---|---|---|---|---|
| Carbohydrate Substrates | 1 | 2 | 3 | 4 | 5 | 6 | 7 | 8 | 9 | 10 | 11 |
| Adonitol | + | − | − | − | − | + | − | − | − | − | − |
| Arabinose | + | + | + | + | + | + | + | − | − | + | + |
| Dulcitol | − | − | − | − | − | − | − | − | − | − | − |
| Fructose | + | + | + | + | + | + | + | + | + | + | + |
| Glycerol | + | + | − | − | + | + | + | − | + | + | + |
| Lactate | − | − | − | − | − | ND | − | − | + | − | − |
| Maltose | + | + | − | − | + | + | + | + | + | + | + |
| Mannose | + | + | − | − | + | + | + | + | + | + | + |
| Melibiose | + | − | + | − | − | + | + | − | − | + | − |
| Raffinose | − | − | − | + | + | − | + | − | + | + | − |
| Ribose | + | + | + | + | + | + | + | + | + | − | + |
| Sorbitol | + | + | + | − | + | + | + | − | + | + | + |
| Sucrose | + | + | + | + | + | + | + | + | + | + | − |
| Xylose | + | + | − | + | + | + | + | + | + | + | + |
| Amygdalin | + | + | + | + | + | + | − | + | − | − | − |
| Cellobiose | + | + | + | + | + | − | − | + | + | − | + |
| Erythritol | − | − | − | − | − | + | − | − | − | − | − |
| Glucose | + | + | + | + | + | + | + | + | + | + | + |
| Inositol | + | + | − | − | − | − | − | − | − | − | − |
| Lactose | + | + | + | + | + | + | + | + | − | + | + |
| Mannitol | + | + | + | + | + | + | + | + | + | + | + |
| Melezitose | + | + | + | + | + | + | − | − | − | − | − |
| Pyruvate | + | − | − | − | − | − | + | − | − | − | − |
| Rhamnose | + | − | + | + | − | + | + | − | + | + | + |
| Salicin | + | + | + | + | + | + | + | + | − | + | + |
| Starch | + | − | − | − | + | + | − | + | − | − | − |
| Trehalose | + | + | + | + | + | + | − | + | + | + | + |

TABLE 5B

Carbohydrate Fermentation Tests

| Carbohydrates Substrate | Bacterium (isolate) | | | | | | | | | | |
|---|---|---|---|---|---|---|---|---|---|---|---|
| | 12 | 13 | 14 | 15 | 16 | 17 | 18 | 19 | 20 | 21 | 22 |
| Adonitol | − | − | − | − | − | − | − | − | − | | |
| Arabinose | + | − | − | + | + | + | + | − | − | | |
| Dulcitol | − | − | − | − | − | − | − | − | − | | |
| Fructose | + | − | + | + | + | + | − | − | + | | |
| Glycerol | + | − | + | + | − | + | − | − | − | | |
| Lactate | − | − | + | + | − | − | − | − | + | | |
| Maltose | + | − | + | + | + | + | + | − | + | | |
| Mannose | + | − | + | + | + | + | − | − | + | | |
| Melibiose | + | − | + | + | + | + | − | − | − | | |
| Raffinose | + | − | − | + | + | + | + | − | + | | |
| Ribose | + | − | + | + | + | + | − | − | + | | |
| Sorbitol | + | − | + | + | + | + | − | − | − | | |
| Sucrose | + | − | + | + | + | + | + | − | + | | |
| Xylose | + | − | − | + | + | + | − | − | + | | |
| Amygdalin | − | − | − | + | + | − | − | − | − | | |
| Cellobiose | − | − | − | + | + | − | + | − | + | | |
| Erythritol | − | − | − | − | − | − | − | − | − | | |
| Glucose | + | − | + | + | + | + | + | − | + | | |
| Inositol | − | − | + | + | − | + | − | − | − | | |
| Lactose | + | − | − | + | + | + | − | − | + | | |
| Mannitol | + | − | + | + | − | + | − | − | + | | |
| Melezitose | − | − | − | + | − | − | − | − | + | | |
| Pyruvate | − | − | − | + | − | − | − | − | + | | |
| Rhamnose | + | − | − | − | + | − | − | − | + | | |
| Salicin | + | − | + | + | + | − | + | − | − | | |
| Starch | − | − | − | + | + | − | − | − | + | | |
| Trehalose | + | − | + | + | + | + | + | − | + | | |

TABLE 5C

Carbohydrate Fermentation Tests

| Carbohydrate Substrates | Bacterium (isolate) | | | | | | |
|---|---|---|---|---|---|---|---|
| | 23 | 24 | 25 | 26 | 27 | 28 | 29 |
| Adonitol | − | − | − | − | − | − | |
| Arabinose | − | + | + | − | − | − | |
| Dulcitol | − | − | − | − | − | − | |
| Fructose | + | + | − | + | + | + | |
| Glycerol | − | − | + | + | − | − | |
| Lactate | − | + | − | − | − | − | |
| Maltose | − | + | + | + | − | + | |
| Mannose | + | − | − | + | − | − | |
| Melibiose | − | − | − | + | − | − | |
| Raffinose | − | + | + | + | − | − | |
| Ribose | − | − | − | − | − | − | |
| Sorbitol | − | − | − | − | − | − | |
| Sucrose | − | + | + | + | − | − | |
| Xylose | + | − | − | + | − | − | |
| Amygdalin | − | + | − | − | − | − | |
| Cellobiose | − | + | − | + | − | + | |
| Erythritol | − | − | − | − | − | − | |
| Glucose | + | + | + | + | − | + | |
| Inositol | − | − | − | − | − | − | |
| Lactose | − | + | + | + | − | + | |
| Mannitol | + | − | − | − | − | − | |
| Melezitose | − | − | − | − | − | − | |
| Pyruvate | − | − | − | − | − | − | |
| Rhamnose | − | − | − | − | − | − | |
| Salicin | − | + | + | − | − | − | |
| Starch | − | − | − | + | − | − | |
| Trehalose | − | + | + | − | − | + | |

TABLE 6

API Rapid STREP System Tests

| Enzyme/Substrate | Bacterium (isolate) | | | | | | | | |
|---|---|---|---|---|---|---|---|---|---|
| | 1 | 2 | 3 | 4 | 5 | 6 | 7 | 8 | 9 |
| Voges-Proskauer | +/+ | +/+ | +/+ | +/+ | +/+ | +/+ | +/+ | +/+ | +/+ |
| Hippurate Hydrolysis | −/− | +/+ | +/+ | +/+ | +/+ | +/+ | +/+ | −/− | −/− |
| Esculin Hydrolysis | +/+ | +/+ | +/+ | +/+ | +/+ | +/+ | +/+ | −/+ | −/− |
| Pyrrolidonyl-2-napthylamide | +/+ | +/+ | +/+ | +/+ | +/+ | +/+ | +/+ | +/+ | −/− |
| Alpha-galactosidase | −/− | −/− | −/− | −/− | −/− | −/− | −/− | −/− | −/− |
| Beta-glucuronidase | −/− | −/− | −/− | −/− | +/+ | −/− | +/+ | −/− | −/− |
| Beta-galactosidase | −/− | +/+ | +/+ | +/+ | +/+ | −/− | +/+ | −/− | −/− |
| Alkaline Phosphatase | −/− | −/− | −/− | −/+ | −/− | −/− | +/+ | −/− | −/− |
| Leucine Arylamidase | +/+ | −/− | +/+ | −/− | +/+ | +/+ | +/+ | +/+ | +/+ |
| Arginine Dihydrolase | +/+ | +/+ | +/+ | +/+ | +/+ | −/− | +/+ | −/+ | −/− |
| Ribose | +/+ | +/+ | +/+ | +/+ | +/+ | +/+ | +/+ | +/+ | −/− |
| Arabinose | −/− | −/− | +/+ | +/+ | +/+ | +/+ | +/+ | −/− | −/− |
| Mannitol | +/+ | +/+ | +/+ | +/+ | +/+ | +/+ | +/+ | +/+ | −/+ |
| Sorbitol | +/+ | +/+ | −/− | −/− | −/− | +/+ | +/+ | −/− | −/− |
| Lactose | −/− | −/− | +/+ | +/+ | +/+ | +/+ | +/+ | +/+ | −/− |
| Trehalose | +/+ | +/+ | +/+ | +/+ | +/+ | +/+ | +/+ | +/+ | −/− |
| Inulin | −/− | −/− | −/− | −/− | −/− | −/− | −/− | −/− | −/− |
| Raffinose | −/− | −/− | −/− | −/− | +/+ | −/− | +/+ | −/− | −/− |
| Starch | +/+ | +/+ | +/+ | −/− | +/+ | −/− | +/+ | −/− | −/− |
| Glycogen | −/− | −/− | −/− | −/− | −/− | −/− | −/− | −/− | −/− |

*Data of replicate 1/replicate 2

TABLE 7

API STAPH Trac System Test

| Enzyme/Substrate | Bacterium (isolate) | | | | | | | | |
|---|---|---|---|---|---|---|---|---|---|
| | 1 | 2 | 3 | 4 | 5 | 6 | 7 | 8 | 9 |
| Glucose | +/+ | +/0 | +/+ | +/+ | +/+ | +/+ | +/+ | +/+ | +/+ |
| Fructose | +/+ | +/+ | +/+ | +/+ | +/+ | +/+ | +/+ | +/+ | +/+ |
| Mannose | +/+ | +/+ | +/+ | +/+ | +/+ | +/+ | +/+ | +/+ | +/+ |
| Maltose | +/+ | +/+ | +/+ | +/+ | +/+ | +/+ | +/+ | +/+ | +/+ |
| Lactose | +/+ | –/– | +/+ | +/+ | +/+ | +/+ | +/+ | +/+ | +/+ |
| Trehalose | +/+ | +/+ | +/+ | +/+ | +/+ | +/+ | +/+ | +/+ | +/+ |
| Mannitol | +/+ | +/+ | +/+ | +/+ | +/+ | +/+ | +/+ | +/+ | +/+ |
| Xylitol | –/– | –/– | –/– | –/– | –/– | +/+ | –/– | –/– | +/+ |
| Melibiose | –/– | –/– | +/+ | +/+ | +/+ | +/+ | +/+ | –/– | +/+ |
| Nitrate Reduction | –/– | –/– | –/– | –/– | –/– | –/– | –/– | +/+ | –/– |
| Alkaline Phosphatase | +/+ | –/– | +/+ | –/– | –/– | –/– | –/– | +/+ | +/+ |
| Acetoin Production | +/+ | +/+ | +/+ | +/+ | +/+ | +/+ | +/+ | +/+ | +/+ |
| Raffinose | –/– | –/– | –/– | –/– | +/+ | +/+ | +/+ | –/– | +/+ |
| Xylose | –/– | –/– | –/– | –/– | +/+ | +/+ | +/+ | +/+ | +/+ |
| Saccharose | +/+ | +/+ | +/+ | +/+ | +/+ | +/+ | +/+ | +/+ | +/+ |
| Alpha-Methyl-Glucoside | +/+ | –/– | –/– | –/– | +/+ | +/+ | +/+ | –/– | +/+ |
| N-Acetyl-Gluoside | +/+ | +/+ | +/+ | +/+ | +/+ | +/+ | +/+ | +/+ | +/+ |
| Arginine Dihydrolase | +/+ | +/+ | +/+ | +/+ | +/+ | –/– | +/+ | +/+ | –/– |
| Urease | –/– | –/– | –/– | –/– | –/– | –/– | –/– | –/– | –/– |

*Data of replicate 1/replicate 2

TABLE 8A

API ZYM Semiquantitative Enzyme System Tests

| Enzyme Assayed | Bacterium (isolate) | | | | | | | | | |
|---|---|---|---|---|---|---|---|---|---|---|
| | 1 | 2 | 3 | 4 | 5 | 6 | 7 | 8 | 9 | 10 |
| Control | 0/0 | 0/0 | 0/0 | 0/0 | 0/0 | 0/0 | 0/0 | 0/0 | 0/0 | 0/0 |
| Alkiline Phosphatase | 0/0 | 1/0 | T/T | T/T | 0/0 | 2/2 | 0/0 | T/T | 0/0 | 5/4 |
| Esterase (C4) | 0/0 | 1/1 | 1/1 | 1/1 | 2/2 | 2/2 | 1/1 | 0/0 | T/T | 0/0 |
| Esterase Lipase (C8) | 1/3 | 2/2 | 2/2 | 2/2 | 2/2 | 0/0 | 2/2 | 2/1 | 2/2 | T/T |
| Lipase (C14) | 0/0 | 0/0 | 0/0 | 0/0 | T/0 | 0/0 | 0/0 | 0/0 | 2/2 | 0/0 |
| Leucine Aminopeptidase | 5/3 | T/1 | 1/1 | 0/0 | 0/0 | 0/0 | 1/1 | 2/3 | 3/3 | 1/1 |
| Valine Aminopeptidase | 0/0 | 0/0 | 0/0 | 0/0 | 0/0 | 0/0 | 0/0 | 0/0 | 2/2 | T/T |
| Cystine Aminopeptidase | T/T | 0/0 | 0/0 | 0/0 | 0/0 | 0/0 | 0/0 | T/T | 1/1 | T/T |
| Trypsin | 0/0 | 0/0 | 0/0 | 0/0 | 0/0 | 0/0 | 0/0 | 0/0 | 0/0 | T/T |
| Chymotrypsin | 0/1 | 0/0 | 0/0 | 0/0 | 2/2 | 0/0 | T/1 | T/T | 0/0 | 0/0 |
| Acid Phosphatase | 3/3 | 1/2 | T/T | 0/0 | 1/1 | 1/1 | 1/1 | 2/3 | 2/2 | 3/3 |
| Phosphohydrolase | 2/2 | 2/2 | 1/1 | 3/3 | 1/1 | 1/1 | 2/2 | 2/2 | 2/2 | 3/3 |
| Alpha-galactosidase | 0/0 | 0/0 | 0/0 | 0/0 | 0/0 | 0/0 | 0/0 | 0/0 | 4/4 | 0/0 |
| Beta-galactosidase | 0/0 | T/T | 0/0 | 0/0 | 0/0 | 0/0 | 1/1 | 1/1 | 3/3 | 2/3 |
| Beta-glucuronidase | 0/0 | 0/0 | 0/0 | 0/0 | 0/0 | 0/0 | 0/0 | 1/1 | 0/0 | 0/0 |
| Alpha-glucosidase | 4/4 | 2/3 | 0/0 | 0/0 | 0/0 | 0/0 | 2/2 | 3/3 | 0/0 | 0/0 |
| Beta-glucosidase | 4/3 | 0/0 | 2/2 | 1/1 | 2/1 | 0/0 | T/T | 2/2 | 0/0 | 0/0 |
| N-acetyl-beta-glucosaminidase | 1/1 | 0/0 | 0/0 | 0/0 | 0/0 | 0/0 | 0/0 | 1/1 | 0/0 | 0/0 |
| Alpha-mannosidase | 0/0 | 0/0 | 0/0 | 0/0 | 0/0 | 0/0 | 0/0 | 0/0 | 0/0 | 0/0 |
| Alpha-fucosidase | 0/0 | 0/0 | 0/0 | 0/0 | 0/0 | 0/0 | 0/0 | 0/0 | 0/0 | 0/0 |

The semiquantitative enzyme activities are scored as follows: 0 = <5 nmol, T (trace) = <5 nmol, 1 = 5 nmol, 2 = 10 nmol, 3 = 20 nmol, 4 = 30 nmol, and 5 ≧ 40 nmol.
*Data of replicate 1/replicate 2

TABLE 8B

API ZYM Semiquantitative Enzyme System Tests

| Enzyme Assayed | Bacterium (isolate) | | | | | | | | | |
|---|---|---|---|---|---|---|---|---|---|---|
| | 11 | 12 | 13 | 14 | 15 | 16 | 17 | 18 | 19 | 20 |
| Control | 0/0 | 0/0 | 0/0 | 0/0 | 0/0 | 0/0 | 0/0 | 0/0 | 0/0 | 0/0 |
| Alkaline Phosphatase | 5/5 | 3/2 | 2/2 | 3/3 | 2/3 | 3/3 | 0/0 | 0/0 | 0/0 | 5/5 |
| Esterase (C4) | 1/1 | 0/0 | 3/3 | 3/3 | 0/0 | 0/0 | 1/1 | 0/0 | 0/0 | 1/1 |

TABLE 8B-continued

API ZYM Semiquantitative Enzyme System Tests

| Enzyme Assayed | Bacterium (isolate) | | | | | | | | | |
|---|---|---|---|---|---|---|---|---|---|---|
| | 11 | 12 | 13 | 14 | 15 | 16 | 17 | 18 | 19 | 20 |
| Esterase Lipase (C8) | 1/1 | 0/0 | 4/3 | 3/3 | 0/0 | T/1 | 1/1 | 0/0 | T/0 | 1/1 |
| Lipase (C14) | 1/T | 1/T | 3/3 | 2/3 | 0/0 | 0/0 | 0/0 | 0/0 | 0/0 | 0/0 |
| Leucine Aminopeptidase | 3/4 | 5/5 | 4/4 | 4/4 | 4/4 | 0/0 | 0/0 | 0/0 | 0/0 | 0/0 |
| Valine Aminopeptidase | 1/1 | 2/3 | 2/2 | 2/2 | 1/1 | 0/0 | 0/0 | 0/0 | 0/0 | 0/0 |
| Cystine Aminopeptidase | T/T | 0/0 | 1/1 | 1/1 | 0/0 | 0/0 | 0/0 | 0/0 | 0/0 | 0/0 |
| Trypsin | T/T | 2/2 | 2/2 | 2/2 | 0/0 | 0/0 | 0/0 | 0/0 | 0/0 | 0/0 |
| Chymotrypsin | T/T | 0/0 | 0/0 | 0/0 | 0/0 | 1/1 | 0/0 | 0/0 | 0/0 | 0/0 |
| Acid Phosphatase | 5/5 | 3/4 | 2/2 | 4/4 | 4/4 | 2/3 | 0/0 | 2/2 | T/T | 2/2 |
| Phosphohydrolase | 4/3 | 3/3 | 1/1 | 2/2 | 4/3 | 2/2 | 1/1 | 2/2 | T/T | 2/2 |
| Alpha-galactosidase | 2/1 | 0/0 | 0/0 | 2/2 | 0/0 | 5/5 | 4/4 | 0/0 | 0/0 | 2/2 |
| Beta-galactosidase | 4/4 | 3/3 | 0/0 | 4/3 | 2/2 | 2/3 | 5/5 | 0/0 | 3/3 | 3/3 |
| Beta-glucuronidase | 1/1 | 0/0 | 0/0 | 1/1 | T/0 | 0/0 | 0/0 | 0/0 | 0/0 | 0/0 |
| Alpha-glucosidase | 1/1 | T/T | 0/0 | 2/2 | 0/0 | 1/1 | 3/4 | 2/2 | 2/3 | 0/0 |
| Beta-glucosidase | 0/0 | 0/0 | 0/0 | 0/0 | 0/0 | 5/5 | 0/0 | 0/0 | 3/3 | 0/0 |
| N-acetyl-beta-glucosaminidase | 0/0 | 0/0 | 0/0 | 2/2 | T/0 | 3/3 | 0/0 | 0/0 | 0/0 | 5/5 |
| Alpha-mannosidase | 0/0 | 0/0 | 0/0 | 0/0 | 0/0 | 0/0 | 0/0 | 0/0 | 0/0 | 0/0 |
| Alpha-fucosidase | 0/0 | 0/0 | 0/0 | 0/0 | 0/0 | 0/0 | 0/0 | 0/0 | 0/0 | 0/0 |

TABLE 8C

API ZYM Semiquantitative Enzyme System Tests

| Enzyme Assayed | Bacterium (isolate) | | | | | | | | |
|---|---|---|---|---|---|---|---|---|---|
| | 21 | 22 | 23 | 24 | 25 | 26 | 27 | 28 | 29 |
| Control | 0/0 | 0/0 | 0/0 | 0/0 | 0/0 | 0/0 | 0/0 | 0/0 | 0/0 |
| Alkaline Phosphatase | 0/0 | 0/0 | 0/0 | 0/0 | 5/5 | T/T | 5/5 | 0/0 | 0/0 |
| Esterase (C4) | T/T | 0/0 | 1/1 | 0/0 | 0/0 | 0/0 | 0/0 | 0/0 | T/T |
| Esterase Lipase (C8) | T/T | 1/1 | 1/1 | T/T | 0/0 | 0/0 | 1/1 | 0/0 | 1/T |
| Lipase (C14) | 0/0 | 0/0 | 0/0 | 0/0 | 0/0 | 0/0 | 0/0 | 0/0 | 0/0 |
| Leucine Aminopeptidase | 0/0 | 0/0 | 0/0 | 0/0 | 0/0 | 0/0 | T/T | 0/0 | 0/0 |
| Valine Aminopeptidase | 0/0 | 0/0 | 0/0 | 0/0 | 0/0 | 0/0 | 0/0 | 0/0 | 0/0 |
| Cystine Aminopeptidase | 0/0 | 0/0 | 0/0 | 0/0 | 0/0 | 0/0 | 0/0 | 0/0 | 0/0 |
| Trypsin | 0/0 | 0/0 | 0/0 | 0/0 | 0/0 | 0/0 | 0/0 | 0/0 | 0/0 |
| Chymotrypsin | 0/0 | 0/0 | 0/0 | 0/0 | 0/0 | 0/0 | 0/0 | 0/0 | 0/0 |
| Acid Phosphatase | 0/0 | T/0 | 0/0 | 0/0 | 2/2 | 1/1 | 4/2 | 2/2 | 1/1 |
| Phosphohydrolase | 1/1 | 1/1 | 1/1 | 2/2 | 1/1 | 1/1 | 5/3 | 2/1 | 2/2 |
| Alpha-galactosidase | 2/2 | T/0 | 2/1 | 0/0 | 0/0 | 0/0 | 4/2 | 0/0 | 1/T |
| Beta-galactosidase | 0/0 | T/0 | 0/0 | 0/0 | 0/0 | 0/0 | 4/2 | 0/0 | 0/0 |
| Beta-glucuronidase | 0/0 | 0/0 | 0/0 | 0/0 | 0/0 | 0/0 | 5/3 | 0/0 | 0/0 |
| Alpha-glucosidase | 0/0 | 3/2 | 1/T | 0/0 | 0/0 | 2/2 | 3/2 | 0/0 | 0/0 |
| Beta-glucosidase | 0/0 | 1/T | 1/T | 0/0 | 2/3 | 0/0 | 0/0 | 0/0 | 0/T |
| N-acetyl-beta-glucosaminidase | 0/0 | 0/0 | 0/0 | 0/0 | 0/0 | 0/0 | 3/2 | 0/0 | 0/0 |
| Alpha-mannosidase | 0/0 | 0/0 | 0/0 | 0/0 | 0/0 | 0/0 | 0/0 | 0/0 | 0/0 |
| Alpha-fucosidase | 0/0 | 1/T | 0/0 | 0/0 | 0/0 | 0/0 | 1/0 | 0/0 | 0/0 |

TABLE 9A

Presumpto Plate System Tests

| Presumtpo Plate No. | Quadrant No. | Agar Media | Growth Ability/ Biochemical Tests | bacterium (isolate) | | | |
|---|---|---|---|---|---|---|---|
| | | | | 16 | 17 | 18 | 19 |
| I | 1 | LD Media | Growth | +++ | +++ | + | |
| | | | Indole | − | − | − | |
| | 2 | LD-Esculin | Growth | +++ | + | +++ | |
| | | | Catalase | − | − | − | |
| | | | Esculin Hydrolysis | +++ | − | − | |
| | 3 | LD-Egg Yolk | Growth | +++ | + | +++ | |
| | | | Lecithinase | − | − | − | |
| | | | Lipase | − | − | − | |
| | | | Proteolysis | − | − | − | |

TABLE 9A-continued

Presumpto Plate System Tests

| Presumpto Plate No. | Quadrant No. | Agar Media | Growth Ability/ Biochemical Tests | bacterium (isolate) 16 | 17 | 18 | 19 |
|---|---|---|---|---|---|---|---|
| | 4 | LD-Bile | Growth | I | I | I | |
| II | 1 | LD-DNA | Growth | +++ | +++ | +++ | |
| | | | DNAse | + | − | − | |
| | 2 | LD-Glucose | Growth | +++ | +++ | +++ | |
| | | | Glucose Fermentation | + | + | − | |
| | 3 | LD-Milk | Growth | +++ | +++ | +++ | |
| | | | Casein Hydrolysis | − | − | − | |
| | 4 | LD-Starch | Growth | +++ | +++ | +++ | |
| | | | Starch Hydrolysis | − | − | − | |
| III | 1 | LD-Mannitol | Growth | +++ | +++ | +++ | |
| | | | Mannitol Fermentation | − | + | − | |
| | 2 | LD-Lactose | Growth | +++ | +++ | +++ | |
| | | | Lactose Fermentation | + | + | − | |
| | 3 | LD-Rhamnose | Growth | +++ | +++ | +++ | |
| | | | Rhamnose Fermentation | + | − | − | |
| | 4 | LD-Gelatin | Growth | +++ | +++ | +++ | |
| | | | Gelatin Hydrolysis | − | − | − | |

Comparative growth on LD-bile agar compared with LD agar: I = less growth; and E = equal growth

TABLE 9B

Presumpto Plate System Tests

| Presumpto Plate No. | Quadrant No. | Agar Media | Growth Ability/ Biochemical Tests | bacterium (isolate) 20 | 21 | 22 | 23 |
|---|---|---|---|---|---|---|---|
| I | 1 | LD Media | Growth | | | | |
| | | | Indole | | | | |
| | 2 | LD-Esculin | Growth | | | | |
| | | | Catalase | | | | |
| | | | Esculin Hydrolysis | | | | |
| | 3 | LD-Egg Yolk | Growth | | | | |
| | | | Lecithinase | | | | |
| | | | Lipase | | | | |
| | | | Proteolysis | | | | |
| | 4 | LD-Bile | Growth | | | | |
| II | 1 | LD-DNA | Growth | | | | |
| | | | DNAse | | | | |
| | 2 | LD-Glucose | Growth | | | | |
| | | | Glucose Fermentation | | | | |
| | 3 | LD-Milk | Growth | | | | |
| | | | Casein Hydrolysis | | | | |
| | 4 | LD-Starch | Growth | | | | |
| | | | Starch Hydrolysis | | | | |
| III | 1 | LD-Mannitol | Growth | | | | |
| | | | Mannitol Fermentation | | | | |
| | 2 | LD-Lactose | Growth | | | | |
| | | | Lactose Fermentation | | | | |
| | 3 | LD-Rhamnose | Growth | | | | |
| | | | Rhamnose Fermentation | | | | |
| | 4 | LD-Gelatin | Growth | | | | |
| | | | Gelatin Hydrolysis | | | | |

TABLE 9C

Presumpto Plate System Tests

| Presumpto Plate No. | Quadrant No. | Agar Media | Growth Ability/ Biochemical Tests | bacterium (isolate) 24 | 25 | 26 | 27 |
|---|---|---|---|---|---|---|---|
| I | 1 | LD Media | Growth | | | | |
| | | | Indole | | | | |
| | 2 | LD-Esculin | Growth | | | | |
| | | | Catalase | | | | |
| | | | Esculin Hydrolysis | | | | |
| | 3 | LD-Egg Yolk | Growth | | | | |
| | | | Lecithinase | | | | |
| | | | Lipase | | | | |
| | | | Proteolysis | | | | |
| | 4 | LD-Bile | Growth | | | | |
| II | 1 | LD-DNA | Growth | | | | |
| | | | DNAse | | | | |
| | 2 | LD-Glucose | Growth | | | | |
| | | | Glucose Fermentation | | | | |
| | 3 | LD-Milk | Growth | | | | |
| | | | Casein Hydrolysis | | | | |
| | 4 | LD-Starch | Growth | | | | |
| | | | Starch Hydrolysis | | | | |
| III | 1 | LD-Mannitol | Growth | | | | |
| | | | Mannitol Fermentation | | | | |
| | 2 | LD-Lactose | Growth | | | | |
| | | | Lactose Fermentation | | | | |
| | 3 | LD-Rhamnose | Growth | | | | |
| | | | Rhamnose Fermentation | | | | |
| | 4 | LD-Gelatin | Growth | | | | |
| | | | Gelatin Hydrolysis | | | | |

TABLE 9D

Presumpto Plate System Tests

| Presumpto Plate No. | Quadrant No. | Agar Media | Growth Ability/ Biochemical Tests | bacterium (isolate) 28 | 29 |
|---|---|---|---|---|---|
| I | 1 | LD Media | Growth | +++ | |
| | | | Indole | − | |
| | 2 | LD-Esculin | Growth | +++ | |
| | | | Catalase | − | |
| | | | Esculin Hydrolysis | − | |
| | 3 | LD-Egg Yolk | Growth | +++ | |
| | | | Lecithinase | − | |
| | | | Lipase | − | |
| | | | Proteolysis | − | |
| | 4 | LD-Bile | Growth | E | |
| II | 1 | LD-DNA | Growth | +++ | |
| | | | DNAse | − | |
| | 2 | LD-Glucose | Growth | +++ | |
| | | | Glucose Fermentation | − | |
| | 3 | LD-Milk | Growth | +++ | |
| | | | Casein Hydrolysis | − | |
| | 4 | LD-Starch | Growth | +++ | |
| | | | Starch Hydrolysis | − | |
| III | 1 | LD-Mannitol | Growth | +++ | |
| | | | Mannitol Fermentation | − | |
| | 2 | LD-Lactose | Growth | +++ | |
| | | | Lactose Fermentation | − | |
| | 3 | LD-Rhamnose | Growth | +++ | |
| | | | Rhamnose Fermentation | − | |
| | 4 | LD-Gelatin | Growth | +++ | |
| | | | Gelatin Hydrolysis | + | |

TABLE 10A

Antimicrobial Susceptibility Test

| Antimicrobial | \multicolumn{10}{c}{Bacterium (isolate)} | | | | | | | | | |
|---|---|---|---|---|---|---|---|---|---|---|
| | 1 | 2 | 3 | 4 | 5 | 6 | 7 | 8 | 9 | 10 |
| Amikacin | R | S | S | S | S | S | S | S | S | S |
| Ampicillin | S | S | S |   | S | S | S | S | S | S |
| Augmentin | S | S | S | R |   | R |   | S |   | S |
| Bacitracin | R | R | R | R | R | S | R | S | S | R |
| Carbenicillin | S | S | S | R | S | R | S | R | S | S |
| Cephaloridine | S | R | S | R | R | S | R | S | S | S |
| Cephalothin | S | S | R | R | S | S | S | S | S | S |
| Chloramphenicol | S | S | S | S | S | S | S | S | S | S |
| Chlortetracycline | R | R | S | S | S | S | R | S | S | S |
| Clindaimycin | R | R | R | R | R | R | S | S | S | R |
| Cloxacillin | R | R | R | R | R | R | R | R | R | R |
| Erythromycin | R | R | S | S | S | S | R | S | S | S |
| Gentamicin | S | S | S | S | S | S | S | S | S | S |
| Kanamycin | R | R | R | R | S | R | R | S | S | S |
| Lincomycin | R | R | R | R | R | R | R | S | S | R |
| Methicillin | R | R | R | R | S | R | S | R | R | R |
| Nalidixic Acid | R | R | R | R | R | R | R | R | S | S |
| Neomycin | S | S | S | S | S | S | R | S | S | S |
| Nitrofurantoin | S | S | S |   | S | S | S | S | S | S |
| Novobiocin | R | R | R |   | S | S | S | R | S |   |
| Penicillin | R | R | R | R | S | S | S | R | S | R |
| Polymyxin B | R | R | R | R | R | R | R | R | S | S |
| Rifampin | S | S | S | S | S | S | S | S | S | S |
| Streptomycin | R | R | R | R | S | R | R | R | S | S |
| Sulfadiazine | R | R | R | R | R | R | R | S | S | S |
| Trimethoprim | R | S | R | R | R | R | S | R | S | S |
| Tetracycline | R | S | S | S | S | S | R | S | S | S |
| Vancomycin | S | S | S | S | S | S | S | S | R | R |

S = Sensitive, R = Resistant

TABLE 10B

Antimicrobial Susceptibility Test

| Antimicrobial | \multicolumn{10}{c}{Bacterium (isolate)} | | | | | | | | | |
|---|---|---|---|---|---|---|---|---|---|---|
| | 11 | 12 | 13 | 14 | 15 | 16 | 17 | 18 | 19 | 20 |
| Amikacin | S | S | S | S | S | R | S | R | R | R |
| Ampicillin | R | S | R | S | S |   |   |   |   |   |
| Augmentin | S | S |   |   |   | R | S | S | S | S |
| Bacitracin | R | R | R | R | R | R | R | R | R | R |
| Carbenicillin | S | S | S | S | S | S | S | S | S | S |
| Cephaloridine | R | S | R | R | R | R | S | S | S | S |
| Cephalothin | R | S | R | R | S | R | S | S | S | S |
| Chloramphenicol | S | S | S | S | S | S | S | S | S | S |
| Chlortetracycline | S | S | S | S | S | S | S | R | R | R |
| Clindaimycin | R | R | R | R | R | S | S | S | S | S |
| Cloxacillin | R | R | R | R | R | R | R | R | R | R |
| Erythromycin | R | S | S | R | S | S | S | R | R | R |
| Gentamicin | S | S | S | S | S | R | S | R | R | R |
| Kanamycin | S | S | S | S | S | R | S | R | R | R |
| Lincomycin | R | R | R | R | R | S | R | R | R | R |
| Methicillin | R | R | R | R | R | R | R | R | R | R |
| Nalidixic Acid | S | S | S | S | S | R | S | R | R | R |
| Neomycin | S | S | S | S | S | R | S | R | R | R |
| Nitrofurantoin | S | S | R | S | S | S |   |   |   |   |
| Novobiocin |   |   |   | R | S | S |   |   |   |   |
| Penicillin | R | R | R | R | R | R | R | S | S | S |
| Polymyxin B | S | S | S | R | S | R | S | R | R | R |
| Rifampin | R | S | S | S | R | S | S | S | S | S |
| Streptomycin | S | S | S | S | S | R | S | R | R | R |
| Sulfadiazine | S | S | S | S | S | S | R | R | R | R |
| Trimethoprim | S | S | R | S | R | R | R | R | R | R |
| Tetracycline | S | S | S | S | S | S |   | R | R | R |
| Vancomycin | R | R | R | R | S | S |   | S | S | S |

TABLE 10C

Antimicrobial Susceptibility Test

| Antimicrobial | \multicolumn{9}{c}{Bacterium (isolate)} | | | | | | | | |
|---|---|---|---|---|---|---|---|---|---|
| | 21 | 22 | 23 | 24 | 25 | 26 | 27 | 28 | 29 |
| Amikacin | R | R | R | R | R | R | R | S | S |
| Ampicillin |   |   |   |   |   |   |   |   |   |
| Augmentin | S | S | S | S | S | S | S | S | S |
| Bacitracin | R | R | R | R | R | R | R | R | R |
| Carbenicillin | S | S | S | S | S | S | S | S | S |
| Cephaloridine | S | S | S | S | S | S | S | S | S |
| Cephalothin | S | S | S | S | S | S | S | S | S |
| Chloramphenicol | S | S | S | S | S | S | S | S | S |
| Chlortetracycline | R | R | R | R | R | R | R | S | S |
| Clindaimycin | S | S | S | S | S | S | S | S | S |
| Cloxacillin | R | R | R | R | R | R | R | R | R |
| Erythromycin | R | R | R | R | R | R | S | S | S |
| Gentamicin | R | R | R | R | R | R | S | S | S |
| Kanamycin | R | R | R | R | R | R | S | S | S |
| Lincomycin | R | R | R | R | R | R | S | S | S |
| Methicillin | R | R | R | R | R | R | R | R | R |
| Nalidixic Acid | R | R | R | R | R | R | S | S | S |
| Neomycin | R | R | R | R | R | R | S | S | S |
| Nitrofurantoin |   |   |   |   |   |   |   |   |   |
| Novobiocin |   |   |   |   |   |   |   |   |   |
| Penicillin | S | S | S | S | S | S | S | R | R |
| Polymyxin B | R | R | R | R | R | R | S | S | S |
| Rifampin | S | S | S | S | S | S | S | S | S |
| Streptomycin | R | R | R | R | R | R | S | S | S |
| Sulfadiazine | R | R | R | R | R | R | R | R | R |
| Trimethoprim | R | R | R | R | R | R | R | R | R |
| Tetracycline | R | R | R | R | R | R | S | R | S |
| Vancomycin | S | S | S | S | S | S | S | R | R |

TABLE 11

Effect of treatment with a characterized culture of cecal bacteria on the concentration of propionic acid in the cecal contents of 3-day old and 10-day old broiler chicks[1]

| Group | Trial 2 | | Trial 3 | | Trial 4 | |
|---|---|---|---|---|---|---|
| | Day 3 | Day 10 | Day 3 | Day 10 | Day 3 | Day 10 |
| Controls | .61 ± .58 | 1.82 ± .61 | .68 ± .60 | 2.46 ± .93 | .54 ± .58 | 2.87 ± 0.88 |

TABLE 11-continued

Effect of treatment with a characterized culture of cecal bacteria on the concentration of propionic acid in the cecal contents of 3-day old and 10-day old broiler chicks[1]

| Group | Trial 2 | | Trail 3 | | Trial 4 | |
|---|---|---|---|---|---|---|
| | Day 3 | Day 10 | Day 3 | Day 10 | Day 3 | Day 10 |
| Treated | 21.28 ± 15.75* | 27.64 ± 10.15* | 16.85 ± 8.14* | 27.10 ± 9.48* | 20.73 ± 10.78* | 47.75 ± 12.4* |

[1]Values are mean ± SD of 10 chicks and μmol/g cecal content
*Significantly different from controls (P < .005)

TABLE 12

Effect of treatment with a characterized culture of cecal bacteria on the concentration of total volatile fatty acids in the cecal contents of 3-day old and 10-day broiler chicks[1]

| Group | Trial 2 | | Trail 3 | | Trial 4 | |
|---|---|---|---|---|---|---|
| | Day 3 | Day 10 | Day 3 | Day 10 | Day 3 | Day 10 |
| Controls | 9.03 ± 2.30 | 73.01 ± 6.43 | 14.03 ± 6.75 | 52.87 ± 16.98 | 16.66 ± 2.71 | 71.95 ± 16.25 |
| Treated | 14.75 ± 5.80** | 80.84 ± 20.69 | 45.60 ± 8.05** | 69.14 ± 23.04* | 50.67 ± 22.59** | 107.03 ± 28.63* |

[1]Values are mean ± SD of 10 chicks and μmol/g cecal content
*Significantly different from controls * = (P < .05); ** = (P < .01)

TABLE 13

Effect of treatment with a characterized culture of cecal bacteria on the number of Salmonella typhimurium in the cecal contents of 10-day old broiler chicks

| Group | $Log_{10}$ Salmonella per gram cecal contents | | | |
|---|---|---|---|---|
| | Trial 1 | Trial 2 | Trial 3 | Trial 4 |
| Control | 6.35 ± 0.99[1] | 6.28 ± 0.53 | 4.11 ± 2.15 | 6.37 ± 0.60 |
| Treated | 0 ± 0* | 0.89 ± 1.50* | 0.27 ± 0.69* | 0.60 ± 0.75* |

[1]Data are expressed as x̄ ± SD of 20 chicks
*Significantly different from controls (P < .005)

TABLE 14

Effect of treatment with a characterized culture of cecal bacteria on the number of 10-day old broiler chicks cecal culture positive for Salmonella typhimurium

| Group | Salmonella culture positive chicks/total (%) | | | |
|---|---|---|---|---|
| | Trial 1 | Trial 2 | Trial 3 | Trial 4 |
| Controls | 20/20 (100) | 20/20 (100) | 18/20 (90) | 20/20 (100) |
| Treated | 0/20 (0)* | 7/20 (35)* | 3/20 (15)* | 8/20 (40)* |

*Significantly different from controls (P < .01)

We claim:

1. A composition for inhibiting Salmonella colonization of fowl comprising populations of substantially biologically pure bacteria, said bacteria comprising substantially all of:

(1) a first *Enterococcus faecalis* strain,
(2) a second *Enterococcus faecalis* strain,
(3) first *Enterococcus faecium* strain,
(4) a second *Enterococcus faecium* strain,
(5) a third *Enterococcus faecium* strain,
(6) *Enterococcus avium*,
(7) a third *Enterococcus faecalis* strain,
(8) *Lactococcus lactis*,
(9) a first Lactobacillus strain,
(10) a first *Escherichia coli* strain,
(11) *Citrobacter freundii*,
(12) a *facultative anaerobic*, gram negative bacillus, belonging to the family Enterobacteriaceae,
(13) a Pseudomonas species,
(14) *Serratia liquefaciens*,
(15) a second *Escherichia coli* strain,
(16) a first Propionibacterium species,
(17) a second Propionbacterium species,
(18) a second lactobacillus strain,
(19) an obligate anaerobic, gram positive bacillus which is a first Bifidobacterium strain or a third Lactobacillus strain,
(20) a third Propionibacterium strain,
(21) a first Eubacterium strain,
(22) a second Eubacterium strain,
(23) an unknown obligate anaerobic, gram positive bacillus designated strain OAGPB-5,

(24) a third Eubacterium strain,

(25) an obligate anaerobic, gram positive bacillus which is a second Bifidobacterium strain or a fourth Lactobacillus strain,

(26) an obligate anaerobic, gram positive bacillus which is a third Bifidobacterium strain or a fifth Lactobacillus strain,

(27) a fourth Propionibacterium strain,

(28) A Veillonella species, and

(29) a Fusobacterium species, in an amount effective for inhibiting Salmonella colonization of fowl.

2. A composition as described in claim 1 wherein said composition comprises ATCC deposit no. 55515.

3. A composition as described in claim 1 comprising twenty-six of said bacteria.

4. A composition as described in claim 1 comprising twenty-seven of said bacteria.

5. A composition as described in claim 1 comprising twenty-eight of said bacteria.

6. A composition as described in claim 1 comprising all of said bacteria.

7. A composition as described in claim 1 further comprising lactose.

8. A composition as described in claim 1 further comprising a coccidiostat that is not active against gram positive bacteria.

9. A composition as described in claim 1, further comprising a carrier.

10. A composition as described in claim 1, wherein said bacteria are encapsulated.

11. A feed product comprising an animal feed in combination with said composition of claim 1.

12. A method for inhibiting Salmonella colonization of fowl comprising administering to said fowl a composition including populations of substantially pure bacteria, said bacteria comprising substantially all of:

(1) a first *Enterococcus faecalis* strain, (2) a second *Enterococcus faecalis* strain, (3) first *Enterococcus faecium* strain, (4) a second *Enterococcus faecium* strain, (5) a third *Enterococcus faecium* strain, (6) *Enterococcus avium*, (7) a third *Enterococcus faecalis* strain, (8) *Lactococcus lactis*, (9) a first Lactobacillus strain,

(10) a first *Escherichia coli* strain,

(11) *Citrobacter freundii*,

(12) a *facultative anaerobic*, gram negative bacillus, belonging to the family Enterobacteriaceae,

(13) a Pseudomonas species,

(14) *Serratia liquefaciens*,

(15) a second *Escherichia coli* strain,

(16) a first Propionibacterium species,

(17) a second Propionbacterium species,

(18) a second lactobacillus strain,

(19) an obligate anaerobic, gram positive bacillus which is a first Bifidobacterium strain or a third Lactobacillus strain,

(20) a third Propionibacterium strain,

(21) a first Eubacterium strain,

(22) a second Eubacterium strain,

(23) an unknown obligate anaerobic, gram positive bacillus designated strain OAGPB-5,

(24) a third Eubacterium strain,

(25) an obligate anaerobic, gram positive bacillus which is a second Bifidobacterium strain or a fourth Lactobacillus strain,

(26) an obligate anaerobic, gram positive bacillus which is a third Bifidobacterium strain or a fifth Lactobacillus strain,

(27) a fourth Propionibacterium strain,

(28) A Veillonella species, and

(29) a Fusobacterium species, wherein said composition is administered in an amount effective for inhibiting Salmonella colonization of the intestine of said fowl.

13. A method as described in claim 12 wherein said composition comprises ATCC deposit no. 55515.

14. A method as described in claim 12 wherein said composition comprises twenty-six of said bacteria.

15. A method as described in claim 12 wherein said composition comprises twenty-seven of said bacteria.

16. A method as described in claim 12 wherein said composition comprises twenty-eight of said bacteria.

17. A method as described in claim 12 wherein said composition comprises all of said bacteria.

18. A method as described in claim 12, wherein said fowl are poultry.

19. A method as described in claim 18, wherein said poultry are selected from the group consisting of chickens, turkeys, ducks, quail and geese.

20. A method as described in claim 18, wherein said poultry are less than about 14 days old.

21. A method as described in claim 12, further comprising administering lactose to said fowl.

22. A method as described in claim 12, further comprising administering a coccidiostat that is not substantially active against gram positive bacteria.

23. A method as described in claim 12, wherein said populations of bacteria are administered with a carrier.

24. A method as described in claim 12, wherein said bacteria are encapsulated.

25. A method as described in claim 12, wherein the step of administering comprises orally administering said populations to said fowl.

26. A method as described in claim 25, wherein the step of administering comprises providing said populations in combination with feed for said fowl.

27. A method as described in claim 25, wherein the step of administering comprises providing said populations in combination with water for said fowl.

28. A method as described in claim 12, wherein the step of administering comprises spraying said populations onto said fowl.

29. A method as described in claim 12, wherein the step of administering comprises contacting said populations with the cloaca of said fowl.

\* \* \* \* \*